US007794702B2

(12) United States Patent
Rosen et al.

(10) Patent No.: US 7,794,702 B2
(45) Date of Patent: Sep. 14, 2010

(54) MESENCHYMAL STEM CELLS AS A VEHICLE FOR ION CHANNEL TRANSFER IN SYNCYTIAL STRUCTURES

(75) Inventors: Michael R. Rosen, New York, NY (US); Richard B. Robinson, Cresskill, NJ (US); Ira S. Cohen, Stony Brook, NY (US); Peter Brink, Setauket, NY (US)

(73) Assignees: The Trustees of Columbia University in the City of New York, New York, NY (US); The Research Foundation of State University of New York, Albany, NY (US)

( * ) Notice: Subject to any disclaimer, the term of this patent is extended or adjusted under 35 U.S.C. 154(b) by 664 days.

(21) Appl. No.: 10/342,506

(22) Filed: Jan. 15, 2003

(65) Prior Publication Data

US 2004/0137621 A1 Jul. 15, 2004

(51) Int. Cl.
*A61K 48/00* (2006.01)
(52) U.S. Cl. .................... 424/93.21; 424/93.1; 424/93.2
(58) Field of Classification Search ........................ None
See application file for complete search history.

(56) References Cited

U.S. PATENT DOCUMENTS

| 5,591,625 | A | 1/1997 | Gerson et al. |
| 6,387,369 | B1 | 5/2002 | Pittenger et al. |
| 6,852,704 | B1 | 2/2005 | Levy et al. |
| 6,979,532 | B2 * | 12/2005 | Jansen et al. ............ 435/4 |
| 7,494,644 | B2 * | 2/2009 | Lee ..................... 424/93.21 |
| 2004/0254134 | A1 | 12/2004 | Marban et al. |

FOREIGN PATENT DOCUMENTS

WO    WO 02/098286 A2    12/2002

OTHER PUBLICATIONS

Rosen et al Cardio. Res. 64:12-23, 2004.*
Jihong Qu et al., HCN2 Channel Overexpression in Rat Ventricle via Adenovirus-Mediated Gene Transfer, Circulation, vol. 104, Oct. 2001. p. II-133.
Arjang Ruhparwar et al., Transplanted fetal cardiomyocytes as cardiac pacemarker, European Journal of Cardio-thoracic Surgery, vol. 21. May 2002, pp. 853-857.
Catalin Toma et al., Human Mesenchymal Stem Cells Differentiate to a Cardiomyocyte Phenotype in the Adult Murine Heart, Circulatin, vol. 105, Jan. 2002, pp. 93-98.
Bodo E. Strauer, Repair of Infracted Myocardium by Autologous Intracoronary Mononuclear Bone Marrow Cell Transplatation in Humans, Circulation, vol. 106, Oct. 2002, pp. 1913-1918.
L. Vaca et al., Mutations in the S4 domain of a pacemarker channel alter its voltage dependence, FEBS Letters, vol. 479, Aug. 2000, pp. 35-40.
Alexei Plotnikov et al., Human Mesenchymal Stem Cells Transfected with HCN2 as a Gene Delivery System to Induce Pacemaker Function in Canine Heart, Circulation, vol. 108, Oct. 2003, p. IV-547.
Potapova, I. et al., Human Mesenchymal Stem Cells as a Gene Delivery System to Create Cardiac Pacemakers, Circ Res. Apr. 2004, vol. 94, No. 7, pp. 952-959.
Rosen, Michael et al., Genes stem cells and biological pacemakers, Cardiovasc Res. Oct. 2004, vol. 64, No. 1, pp. 12-23.
Qu, J. et al., Expression and function of a biological pacemaker in canine heart. Circulation, Mar. 2003, vol. 107, No. 8, pp. 1106-1109.
DiFrancesco D: The cardiac hyperpolarizing-activated current, $I_f$: Origins and developments. *Prog. BiophysMol. Biol.* vol. 46, No. 3, 1985, pp. 163-183; (Exhibit 2).
Zhou Z and Lipsius SL: Effect of isoprenaline on $I_f$ current in latent pacemaker cells isolated from cat right atrium: ruptured vs. perforated patch whole-cell recording methods. *Pflugers Arch.* vol. 423, No. 5 Pt. 6, Jun. 1993, pp. 442-447; (Exhibit 3).
Thuringer D, et al.: A hyperpolarization-activated inward current in human myocardial cells. *JmolCell. Cardiol.* vol. 24, No. 5, May 1992, pp. 451-455; (Exhibit 4).
Rosen, M.R. and Robinson R.B.: Heart rate: a simple yet complex concept. *Dialogues in Cardiovascular Medicine*. vol. 6, No. 1, 2001, pp. 2-19; (Exhibit 5).
Yu H, et al.: Pacemaker current exists in ventricular myocytes. *Circ. Res.* vol. 72, No. 1, Jan. 1993, pp. 232-236.; (Exhibit 6).
Cerbai E, et al.: The properties of the pacemaker current $I_f$ in Human Ventricular Myocytes are modulated by Cardiac Disease. *Jmol. Cell Cardiol.* vol. 33, No. 3, Mar. 2001, pp. 441-448; (Exhibit 7).
Yu, H. et al.: MinK-Related Peptide 1: A β Subunit for the HCN Ion Channel Subunit Family Enhances Expression and Speeds Activation. *Cir. Res.* vol. 88, 2001, pp. 84-87; (Exhibit 8).
Robinson RB, et al.: Developmental change in the voltage dependence of the pacemaker current, $I_f$, in rat ventricle cells. *Pflugers Arch.* vol. 433, 1991, pp. 533-535; (Exhibit 9).
Fares N, et al.: Characterization of a hyperpolarization-activated current in dedifferentiated adult rat ventricular cells in primary culture. *J. Physiol.* vol. 506, No. 1, Jan. 1, 1998, pp. 73-82; (Exhibit 10).
Cerbai E, et al.: Influence of postnatal-development on $I_f$ occurrence and properties in neonatal rat ventricular myocytes. *Cardiovasc. Res.* vol. 42, No. 2, May 1999, pp. 416-423; (Exhibit 11).
Cerbai E, et al.: Characterization of the hyperpolarization-activated current, $I_f$, in ventricular myocytes isolated from hypertensive rats. *J. Physiol.* vol. 481, No. 3, Dec. 15, 1994, pp. 585-591; (Exhibit 12).

(Continued)

*Primary Examiner*—Q. Janice Li
(74) *Attorney, Agent, or Firm*—Kenyon & Kenyon LLP

(57) ABSTRACT

This invention provides a composition for delivery of a gene to a syncytial structure comprising stem cells incorporated with the gene. This invention also provides a composition for ion channel transfer which comprises stem cells incorporated with a compound in an amount sufficient to create ion channels. This invention also provides for a method of expressing a functional gene product in a syncytial structure comprising administering a composition, comprising stem cells that have been incorporated with a gene, to the syncytial structure. This invention further provides a method of expressing a functional ion channel in a syncytial structure comprising administering a composition, comprising stem cells that have been incorporated with a compound in an amount sufficient to create ion channels, to the syncytial structure. This invention also provides a composition for delivery of small molecules comprising stem cells incorporated with the small molecules or genes encoding the small molecules.

16 Claims, 20 Drawing Sheets

OTHER PUBLICATIONS

Cerbai E, et al.: Characterization of the hyperpolarization-activated current, $I_f$, in ventricular myocytes from human failing heart. *Circulation*. vol. 95, No. 3, Feb. 4, 1997, pp. 568-571; (Exhibit 13).

Santoro B, et al.: Interactive cloning with the SH3 domain of N-src identifies a new brain specific ion channel protein, with homology to Eag and cyclic nucleotide-gated channels. *Proc. Natl. Sci. USA*. vol. 94, No. 26, Dec. 23, 1997, pp. 14815-14820; (Exhibit 14).

Ludwig A, et al.: A family of hyperpolarization-activated mammalian cation channels. *Nature*. vol. 393, No. 6685, Jun. 11, 1998, pp. 587-591; (Exhibit 15).

Santoro B, et al.: Identification of a gene encoding a hyperpolarization-activated pacemaker channel of brain. *Cell*. vol. 93, No. 5, May 29, 1998, pp. 717-729; (Exhibit 16).

Shi W, et al.: Distribution and Prevalence of hyperpolarization-activated cation channel (HCN) mRNA Expression in Cardiac Tissues. *Circ. Res.* vol. 85, No. 1, Jul. 9, 1999, pp. e1-e6; (Exhibit 17).

Ishii TM, et al.: Molecular characterization of the hyperpolarization-activated cation channel in rabbit heart sinoatrial node: *J. Biol. Chem.* vol. 264, No. 18, Apr. 30, 1999, pp. 12835-12839; (Exhibit 18).

Ludwig A, et al.: Two pacemaker channels from human heart with profoundly different activation kinetics. *EMBO J*. vol. 18, No. 9, May 4, 1999, pp. 2323-2329; (Exhibit 19).

Moosmang S, et al.: Cellular expressing and functional characterization of four hyperpolarization-activated pacemaker channels in cardiac and neuronal tissues. *Eur. J. Biochem*. vol. 268, No. 6, Mar. 2001, pp. 1646-1652; (Exhibit 20).

Qu, J. et al.: Functional Comparison of HCN isoforms expressed in ventricular and HEK 293 cells. *Pfulgers Arch.—Eur. J. Physiol*. vol. 444, 2002, pp. 597-601; (Exhibit 21).

Protas L, et al.: Chronic neuropeptide Y exposure increases L-type Ca current in neonatal rat cardiomyocytes. *Am. J. Physiol*. vol. 277, No. 3 Pt. 2, Sep. 1999, pp. H940-H946. (Exhibit 22).

Kuznetsov V, et al.: β 2-adrenergic receptor actions in neonatal and adult rat ventricular myocytes. *Circ. Res*. vol. 76, No. 1, Jan. 1995, pp. 40-52; (Exhibit 23).

Qu, J. et al.: Sympathetic innervation alters activation of pacemaker current ($I_f$) in rat ventricle. *J. of Physiol*. vol. 526, No. 3, 2000, pp. 561-569; (Exhibit 24).

Ng P, et al.: An enhanced system for construction of adenoviral vectors by the two-plasmid rescue method. *Hwn.Gene Ther*. vol. 11, No. 5, Mar. 20, 2000, pp. 693-699; (Exhibit 25).

He TC, et al.: A simplified system for generating recombinant adenoviruses. *Proc. Natl. Acad. Sci. USA*. vol. 95, No. 5, Mar. 3, 1998, pp. 2509-2514; (Exhibit 26).

Santoro B, et al.: The HCN gene family: molecular basis of the hyperpolarization-activated pacemaker channels. *Ann. NY Acad. Sci*. vol. 868, Apr. 30, 1999, pp. 741-764; (Exhibit 27).

Hamm, A. et al.: Efficient Transfection Method for Primary Cells. *Tissue Engineering*. vol. 8, No. 2, 2002, pp. 235-245; (Exhibit 28).

Hansen JE, et al.: Prediction of O-glycosylation of mammalian proteins: Specificity patterns of UDP-GalNAc:polypeptide N-acetylgalactosaminyltransferase. *Biochem. J*. vol. 308, No. 3, Jun. 15, 1995, pp. 801-813; (Exhibit 29).

Cui J, et al.: Gating of IsK expressed in Xenopus oocytes depends on the amount of mRNA injected. *Gen. Physiol*. vol. 104, No. 1, Jul. 1994, pp. 87-105; (Exhibit 30).

Guillemare E, et al.: Effects of the level of mRNA expression on biophysical properties, sensitivity to neurotoxins, and regulation of the brain delayed-rectifier K+ channels Kv1.2. *Biochemistry*. vol. 31, No. 49, Dec. 15, 1992, pp. 12463-12468; (Exhibit 31).

Honore E, et al.: Different types of K+ channel current are generated by different levels of a single mRNA. *EMBO J*. vol. 11, No. 7, Jul. 1992, pp. 2465-2471; (Exhibit 32).

Qu, J. et al.: HCN2 Overexpression in Newborn and Adult Ventricular Myocytes. *Circ. Res*. vol. 89, 2001, pp. 8-14; (Exhibit 33).

DiFrancesco D, et al.: Direct activation of cardiac pacemaker channels by intracellular cyclic AMP. *Nature*. vol. 351, No. 6322, May 9, 1991, pp. 145-147; (Exhibit 34).

Kaupp UB, et al.: Molecular diversity of pacemaker ion channels. *Annu, Rev. Physiol*. vol. 63, 2001, pp. 235-257; (Exhibit 35).

Chang F, et al.: Effects of protein kinase inhibitors on canine Purkinje fibre pacemaker depolarization and the pacemaker current $I_f$. *J. Physiol*. vol. 440, 1991, pp. 367-384; (Exhibit 36).

Yu H, et al.: Phosphatase inhibition by calyculin A increases $I_f$ in canine Purkinje fibers and myocytes. *Pflugers Arch*. vol. 422, No. 6, Mar. 1993, pp. 614-616; (Exhibit 37).

Schagger H and von Jagow G: Tricine-sodium dodecyl sulfate-polyacrylamide gel electrophoresis for separation of proteins in the range from 1 to 100 Kda. *Analytical Biochem*. vol. 166, No. 2, Nov. 1, 1987, pp. 368-379; (Exhibit 38).

Ranjan R, et al.: Mechanism of anode break stimulation in the heart. *Biophys. J*. vol. 74, No. 4, Apr. 1998, pp. 1850-1863; (Exhibit 39).

Moroni A, et al.: Kinetic and ionic properties of the human HCN2 pacemaker channel. *Pflugers Arch*. vol. 439, No. 5, Mar. 2000, pp. 618-626; (Exhibit 40).

Santoro B, et al.: Molecular and functional heterogeneity of hyperpolarization-activated pacemaker channels in the mouse CNS. *Jneurosci*. vol. 20, No. 14, Jul. 15, 2000, pp. 5264-5275; (Exhibit 41).

Valiunas, V.: Biophysical properties of connexin-45 gap junction hemichannels studied in vertebrate cells. *J. Gen. Physiol*. vol. 119, No. 2, 2002, pp. 147-164; (Exhibit 42).

Melman YF, et al.: Structural determinants of KvLQT1 control by the KCNE family of proteins. *J Biol Chem*. vol. 276, No. 9, Mar. 2, 2001, pp. 6439-6444; (Exhibit 43).

Tinel N, et al.: KCNE2 confers background current characteristics to the cardiac KCNQ1 potassium channel. *EMBO J*. vol. 19, No. 23, Dec. 1, 2000, pp. 6326-6330; (Exhibit 44).

Martens JR, et al.: Differential targeting of Shaker-like potassium channels to lipid rafts. *BiolChem*. vol. 275, No. 11, Mar. 17, 2000, pp. 7443-7446; (Exhibit 45).

Chauhan VS, et al.: Abnormal cardiac Na(+) channel properties and QT heart rate adaptation in neonatal ankyrin(B) knockout mice. *Circ. Res*. vol. 86, No. 4, Mar. 3, 2000, pp. 441-447; (Exhibit 46).

Cao, F. et al.: A quantitative analysis of connexin-specific permeability differences of gap junctions expressed in HeLa transfectants and Xenopus oocytes. *J. Cell Sci*. vol. 111 (pt. 1), 1998, pp. 31-43; (Exhibit 47).

Gerhardstein BL, et al.: Proteolytic processing of the C terminus of the alpha (1C) subunit of L-type calcium channels and role of a proline-rich domain in membrane tethering of proteolytic fragments. *J Biol. Chem*. vol. 275, No. 12, Mar. 24, 2000, pp. 8556-8563; (Exhibit 48).

Barbuti A, et al.: Action of internal pronase on the f-channel kinetics in the rabbit SA node. *J. Physiol*. vol. 520, No. 3, Nov. 1, 1999, pp. 737-744; (Exhibit 49).

Wahler GM: Developmental increases in the inwardly rectifying potassium current of rat ventricular myocytes. *Am. J. Physiol*. vol. 262, No. 5 Pt. 1, May 1992, pp. C1266; (Exhibit 50).

Sanguinetti MC, et al.: Coassembly of KvLGQT1 and minK ($I_{SK}$) proteins to form cardiac $I_{SK}$ potassium channels. *Nature*. vol. 384, No. 6604, Nov. 7, 1996, pp. 80-83; (Exhibit 51).

Dixon JE and McKinnon D: Quantitative analysis of potassium channel expression in atrial and ventricular muscle of rats. *Circ. Res*. vol. 75, No. 2, Aug. 1994, pp. 252-260; (Exhibit 52).

Abbott GW, et al.: MiRP1 forms $I_{kr}$ potassium channels with HERG and is associated with cardiac arrhythmia. *Cell*. vol. 97, No. 2, Apr. 16, 1999, pp. 175-187; (Exhibit 53).

Altomare C, et al.: Integrated allosteric model of voltage gating of HCN channels. *J.Gen. Physiol*. vol. 117, No. 6, 2001, pp. 519-532; (Exhibit 54).

Valiunas, V. et al.: Cardiac gap junction channels show quantitative differences in selectivity. *Circ. Res*. vol. 91, No. 2, 2002, pp. 104-111; (Exhibit 55).

Accili EA, et al.: Properties and modulation of $I_f$ in newborn versus adult cardiac SA node. *Am. J. Physiol*. vol. 272, 1991, pp. H1549-H1552; (Exhbit 56).

Accili EA, et al.: Differential control of the hyperpolarization-activated current ($I_f$) by intracellular cAMP and phosphatase inhibition. *J. Physiol*. vol. 491, 1996, pp. 643-651; (Exhibit 57).

Wainger BJ, et al.: Molecular mechanism of cAMP modulation of HCN pacemaker channels. *Nature*. vol. 411, No. 6839, 2001, pp. 805-810; (Exhibit 58).

Ellingsen O, et al.: Adult rat ventricular myocytes cultured in defined medium: phenotype and electromechanical function. *Am. J. Physiol.* vol. 265, No. 2 Pt. 2, Aug. 1993, pp. H747-H754. (Exhibit 59).

Ruhparwar, A. et al "Transplanted fetal Cardiomyocytes as cardiac pacemaker" EP J. of Cardio-Thoracic Surgery, vol. 21, (2002) pp. 853-857.

Wang, Jih-Shiuan et al. "Marrow stromal cells for celluar cardiomyoplasty: feasibility and potential clinical advantages" The J. of Thoracic and Cardiovascular Surgery, vol. 12:5 (Nov. 2000) pp. 999-1006.

Studeny, M. et al., "Bone Marrow-derived Mesenchymal Stem Cells as Vehicles for Interferon-Beta Delivery into Tumors", Cancer Research (2002), vol. 62, pp. 3603-3608.

Lee, K. et al., "Human Mesenchymal Stem Cells Maintain Transgene Expression during Expansion and Differentiation", Molecular Therapy (2001), vol. 3:6, pp. 857-866.

Chen, J. et al., "The S4-S5 Linker Couples Voltage Sensing and Activation of Pacemaker Channels", PNAS USA (2001), vol. 98:20, pp. 11277-11282.

Ballas, C. B., et al., "Adult Bone Marrow Stem Cells for Cell and Gene Therapies: Implications for Greater Use", J. Cell. Biochem. Suppl. (2002), vol. 38, pp. 20-28.

Advisory Action from U.S. Appl. No. 10/757,827 mailed May 11, 2010.

* cited by examiner

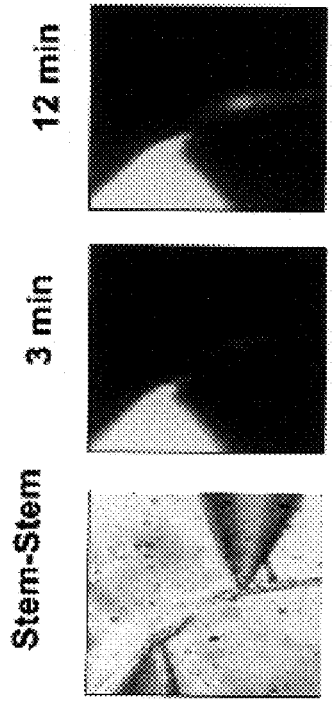
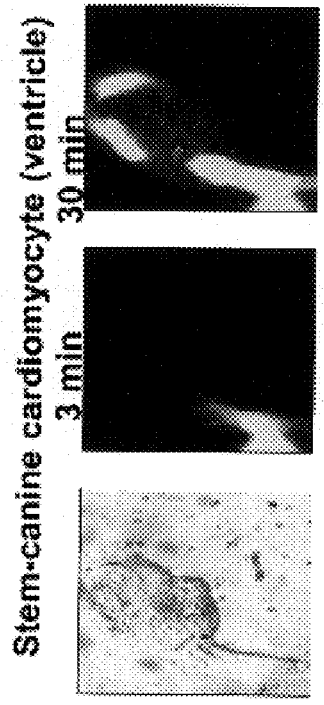
FIGURE 3B
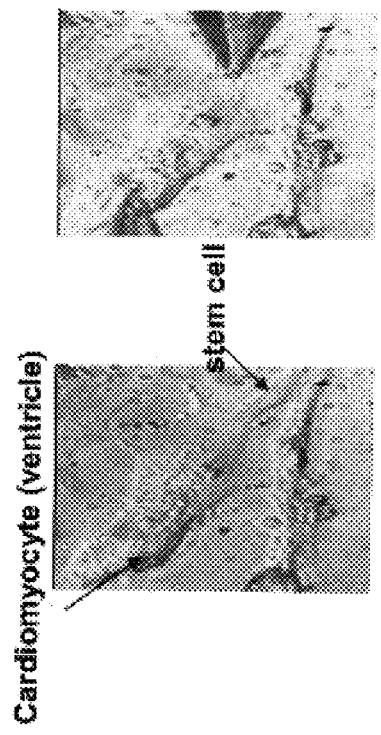
FIGURE 3A
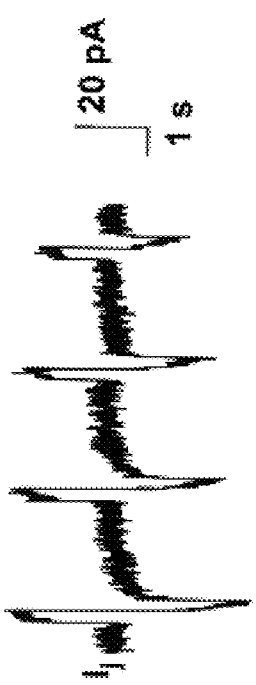
FIGURE 3C

FIGURE 7  HMSC cells transiently transfected with mH2-EGFP

MESENCHYMAL STEM CELLS AS A VEHICLE FOR ION CHANNEL TRANSFER IN SYNCYTIAL STRUCTURES

STATEMENT REGARDING SPONSORED RESEARCH OR DEVELOPMENT

The invention disclosed herein was made with Government support under NIH Grant Nos. HL-28958 and HL-20558 from the National Institutes of Health. Accordingly, the U.S. Government has certain rights in this invention.

BACKGROUND OF THE INVENTION

The present invention relates to mesenchymal stem cells as a vehicle for ion channel transfer in syncytial structures.

Throughout this application, various publications are referenced to by numbers. Full citations may be found at the end of the specification immediately preceding the claims. The disclosures of these publications in the entireties are hereby incorporated by reference into this application in order to more fully describe the state of the art to those skilled therein as of the date of the invention described and claimed herein.

The pacemaker current, $I_f$, is present in both automatic (1) and non-automatic (2-6) regions of the heart. Further, the threshold voltage of activation varies widely among cardiac regions, being least negative in the sinus node (e.g. in rabbit sinus node it is $-40$ mV (7)) and most negative in the ventricle ($-108$ mV or more negative, depending on species (5,8,9)). Interestingly, the current activates at less negative voltages in the newborn ventricle (approximately $-70$ mV in rat (8,10)) and the diseased adult ventricle (approximately $-70$ mV threshold in aged hypertensive rat (11), $-55$ mV in failing human ventricle (12)). The molecular and cellular bases for the regional variability of activation voltages in the normal adult heart and the regulation of ventricular activation voltage by development and disease remain to be determined, but such understanding is critical to any future therapeutic application of the expressed current in myocardium.

Currently, only electronic pacemakers and cardioactive drugs are used to repair cardiac function. There is a need for a biological pacemaker in the heart that utilizes components native to the heart itself, such as alpha and beta subunits of pacemaker channel genes. (57,58,59). The present invention is directed towards perfecting a delivery system for these genes that neither requires the implantation of electronic devices, as in electronic pacemakers, nor the administration of potentially toxic chemicals, as in cardioactive drugs.

SUMMARY OF THE INVENTION

The present invention involves utilizing mesenchymal stem cells as vehicles for gene delivery to syncytial structures. Mesenchymal stem cells, incorporated with genes, are administered to syncytial structures, where the stem cells couple with the syncytia, allowing gene expression to occur within the syncytial structure. For example, ion channel genes delivered via stem cells to the cardiac region can alter cardiac pacemaker activity. Additionally, mesenchymal stem cells can also be similarly used to deliver small molecules to functional syncytia.

The present invention provides a composition for delivery of a gene to a syncytial structure comprising stem cells incorporated with the gene.

The present invention also provides a composition for ion channel transfer which comprises stem cells incorporated with a compound in an amount sufficient to create ion channels.

This invention further provides for a method of expressing a functional gene product in a syncytial structure comprising administering a composition, comprising stem cells that have been incorporated with a gene, to the syncytial structure.

This invention provides for a method of expressing a functional ion channel in a syncytial structure comprising administering a composition, comprising stem cells that have been incorporated with a compound in an amount sufficient to create ion channels, to the syncytial structure.

This invention also provides for a method of treating a cardiac condition in a subject which comprises contacting a cell of the heart of the subject with a composition, comprising stem cells that have been incorporated with a compound in an amount sufficient to create ion channels, in an amount sufficient to increase the current expression of the cell, thereby treating the cardiac condition in the subject.

This invention further provides for a method of inducing a current in the heart in a subject which comprises contacting a cell of the heart of a subject with a composition, comprising stem cells that have been incorporated with a compound in an amount sufficient to create ion channels, in a sufficient amount to induce a current in the cell of the heart of the subject, thereby inducing a current in the cell of the heart of the subject.

This invention also provides for a method of increasing the heart rate in a subject which comprises contacting a cell of the heart of a subject with a composition, comprising stem cells that have been incorporated with a compound in an amount sufficient to create ion channels, in an amount sufficient to decrease the time constant of activation of the cell of the heart, thereby increasing heart rate in the subject.

This invention also provides for a method of inducing a current in a cell which comprises contacting a cell with a composition, comprising stem cells that have been incorporated with a compound in an amount sufficient to create ion channels, in a sufficient amount to induce a current in the cell, thereby inducing a current in the cell.

This invention further provides for a method of causing a contraction of a cell which comprises contacting the cell with a composition, comprising stem cells that have been incorporated with a compound in an amount sufficient to create ion channels, in an amount sufficient to induce a current required to cause a contraction of the cell, thereby causing a contraction of the cell.

This invention also provides for a method of shortening the time required to activate a cell which comprises contacting a cell with a composition, comprising stem cells that have been incorporated with a compound in an amount sufficient to create ion channels, in a sufficient amount to decrease the time constant of activation of the cell, thereby shortening the time required to activate the cell.

The present invention also provides for a method of changing the membrane potential of a cell which comprises contacting a cell with a composition, comprising stem cells that have been incorporated with a compound in an amount sufficient to create ion channels, in a sufficient amount to change the membrane potential of the cell, thereby changing the membrane potential of the cell.

This invention also provides a cardiac myocyte developed from mesenchymal stem cells transformed with a gene.

This invention further provides a composition for delivery of small molecules comprising stem cells incorporated with the small molecules or genes encoding the small molecules.

BRIEF DESCRIPTION OF THE FIGURES

FIGS. 3A-C: coupling and ionic and dye transfer between stem cells and between a stem cell and a canine cardiomyocyte (ventricle). A: light micrograph and fluorescence images of dye transfer between stem cells. B: light micrograph and fluorescence images of dye transfer between a stem cell and a canine cardiomyocyte. C: graph representing ionic transfer between a stem cell and canine cardiomyocyte.

FIG. 7: human mesenchymal stem cells transiently transfected with mH2-EGFP.

DETAILED DESCRIPTION OF THE INVENTION

Figure 1A:
FIGS. 1A-B: stem cells loaded with Lucifer Yellow dye via electroporation. A: light micrograph image of the stem cells. B: fluorescence image of same stem cells. Note the load concentration was 2 mM Lucifer Yellow in media.

The present invention provides a composition for delivery of a gene to a syncytial structure comprising stem cells incorporated with the gene.

In a preferred embodiment of the above-described composition, the stem cells are mesenchymal stem cells.

In a preferred embodiment of the above-described composition, the gene encodes MiRP1.

In a preferred embodiment of the above-described composition, the gene encodes a HCN channel.

In a preferred embodiment of the immediately preceding composition, the HCN channel is HCN1.

In a preferred embodiment of the preceding composition, the HCN channel is HCN2.

In a preferred embodiment of the preceding composition, the HCN channel is HCN4.

In a preferred embodiment of the above-described composition, the gene encodes a mutated HCN channel.

In a preferred embodiment of the immediately preceding composition, the mutated HCN channel is E324A-HCN2.

In a preferred embodiment of the preceding composition, the mutated HCN channel is Y331A-HCN2.

In a preferred embodiment of the preceding composition, the mutated HCN channel is Y331A,E324A-HCN2.

In a preferred embodiment of the above-described composition, the gene encodes MiRP1 and a HCN channel.

In a preferred embodiment of the immediately preceding composition, the HCN channel is HCN1.

In a preferred embodiment of the preceding composition, the HCN channel is HCN2.

In a preferred embodiment of the preceding composition, the HCN channel is HCN4.

In a preferred embodiment of the above-described composition, the gene encodes MiRP1 and a mutated HCN channel.

In a preferred embodiment of the immediately preceding composition, the mutated HCN channel is E324A-HCN2.

In a preferred embodiment of the preceding composition the mutated HCN channel is Y331A-HCN2.

In a preferred embodiment of the preceding composition, the mutated HCN channel is Y331A,E324A-HCN2.

The present invention also provides a composition for ion channel transfer which comprises stem cells incorporated with a compound in an amount sufficient to create ion channels.

In a preferred embodiment of the above-described composition, the stem cells are mesenchymal stem cells.

In a preferred embodiment of the above-described composition, the compound comprises a nucleic acid which encodes MiRP1.

In a preferred embodiment of the above-described composition, the compound comprises a nucleic acid which encodes a HCN channel.

In a preferred embodiment of the immediately preceding composition, the HCN channel is HCN1.

In a preferred embodiment of the preceding composition, the HCN channel is HCN2.

In a preferred embodiment of the preceding composition, the HCN channel is HCN4.

In a preferred embodiment of the above-described composition, the compound comprises a nucleic acid which encodes a mutated HCN channel.

In a preferred embodiment of the immediately preceding composition, the mutated HCN channel is E324A-HCN2.

In a preferred embodiment of the preceding composition, the mutated HCN channel is Y331A-HCN2.

In a preferred embodiment of the preceding composition, the mutated HCN channel is Y331A,E324A-HCN2.

In a preferred embodiment of the above-described composition, the compound comprises a nucleic acid which encodes MiRP1 and a HCN channel.

In a preferred embodiment of the immediately preceding composition, the HCN channel is HCN1.

In a preferred embodiment of the preceding composition, the HCN channel is HCN2.

In a preferred embodiment of the preceding composition, the HCN channel is HCN4.

In a preferred embodiment of the above-described composition, the compound comprises a nucleic acid which encodes MiRP1 and a mutated HCN channel.

In a preferred embodiment of the immediately preceding composition, the mutated HCN channel is E324A-HCN2.

In a preferred embodiment of the preceding composition, the mutated HCN channel is Y331A-HCN2.

In a preferred embodiment of the preceding composition, the mutated HCN channel is Y331A,E324A-HCN2.

The present invention further provides for a method of expressing a functional gene product in a syncytial structure comprising administering a composition, comprising stem cells that have been incorporated with a gene, to the syncytial structure.

In a preferred embodiment of the above-described method, the gene product is an ion channel.

In a preferred embodiment of the above-described method, the syncytial structure is a mammalian heart.

In a preferred embodiment of the above-described method, the syncytial structure is a mammalian bladder.

In a preferred embodiment of the above-described method, the syncytial structure is an artery.

In a preferred embodiment of the above-described method, the syncytial structure is an arteriole.

In a preferred embodiment of the above-described method, the syncytial structure is a mammalian liver.

In a preferred embodiment of the above-described method, the syncytial structure is mammalian gastrointestinal tract.

In a preferred embodiment of the above-described method, the syncytial structure is tumor originating from epithelial tissue.

In a preferred embodiment of the above-described method, the syncytial structure is tumor originating from smooth muscle tissue.

The present invention also provides for a method of expressing a functional ion channel in a syncytial structure comprising administering a composition, comprising stem cells that have been incorporated with a compound in an amount sufficient to create ion channels, to the syncytial structure.

In a preferred embodiment of the above-described method, the syncytial structure is a mammalian heart.

The present invention further provides for a method of treating a cardiac condition in a subject which comprises contacting a cell of the heart of the subject with a composition, comprising stem cells that have been incorporated with a compound in an amount sufficient to create ion channels, in an amount sufficient to increase the current expression of the cell, thereby treating the cardiac condition in the subject.

In a preferred embodiment of the above-described method, the current is the pacemaker current.

In a preferred embodiment of the above-described method, the cardiac condition is a cardiac rhythm disorder.

In a preferred embodiment of the above-described method, the cardiac rhythm disorder is selected from a group consisting of at least one of conduction block, complete atrioventricular block, incomplete atrioventricular block and sinus node dysfunction.

In a preferred embodiment of the above-described method, the step of contacting is selected from the group consisting of systemic administration to the structure and injection.

In a preferred embodiment of the immediately preceding method, the administration of contacting is selected from the group comprising topical application to the cells of the structure, microinjection and catheterization.

The present invention further provides for a method of inducing a current in the heart in a subject which comprises contacting a cell of the heart of a subject with a composition, comprising stem cells that have been incorporated with a compound in an amount sufficient to create ion channels, in a sufficient amount to induce a current in the cell of the heart of the subject, thereby inducing a current in the cell of the heart of the subject.

The present invention also provides for a method of increasing the heart rate in a subject which comprises contacting a cell of the heart of a subject with a composition, comprising stem cells that have been incorporated with a compound in an amount sufficient to create ion channels, in an amount sufficient to decrease the time constant of activation of the cell of the heart, thereby increasing heart rate in the subject.

The present invention also provides for a method of inducing a current in a cell which comprises contacting a cell with a composition, comprising stem cells that have been incorporated with a compound in an amount sufficient to create ion channels, in a sufficient amount to induce a current in the cell, thereby inducing a current in the cell.

The present invention also provides for a method of causing a contraction of a cell which comprises contacting the cell with a composition, comprising stem cells that have been incorporated with a compound in an amount sufficient to create ion channels, in an amount sufficient to induce a current required to cause a contraction of the cell, thereby causing a contraction of the cell.

The present invention further provides for a method of shortening the time required to activate a cell which comprises contacting a cell with a composition, comprising stem cells that have been incorporated with a compound in an amount sufficient to create ion channels, in a sufficient amount to decrease the time constant of activation and deactivation of the cell, thereby shortening the time required to activate and deactivate the cell.

The present invention also provides for a method of changing the membrane potential of a cell which comprises contacting a cell with a composition, comprising stem cells that have been incorporated with a compound in an amount sufficient to create ion channels, in a sufficient amount to change the membrane potential of the cell, thereby changing the membrane potential of the cell.

The present invention also provides a cardiac myocyte developed from mesenchymal stem cells transformed with a gene.

The present invention further provides a composition for delivery of small molecules comprising stem cells incorporated with the small molecules or genes encoding the small molecules.

As used herein, the term "syncytial structure" means a structure with gap junction-mediated communication between its cells.

As used herein, the term "cell of a heart" means a cell derived from a heart, either isolated or in culture.

As used herein, the term "cardiac myocytes" means myocytes derived from muscle or conductive tissue of a heart, either isolated or in culture, and capable of initiating a current.

As used herein, the term "membrane potential of the cell" means the transmembrane potential across the plasma membrane of the cell.

As used herein, the term "inducing a current" means causing a cell to produce an electric current.

As used herein, the term "time required to activate a cell" means the time period for activation of the cell.

As used herein, the term "small molecules" means molecules of up to 1200 Daltons and/or with minor diameters of up to 1.2 nanometers.

Methods explaining the above detailed description are set forth below.

The present invention provides pacemaker channel alpha and/or beta subunit genes and a promoter that can be used to create a regulatable pacemaker in cardiac and/or stem cells.

Phase 1: Expression, Regulation and Function of Pacemaker Channel Genes

Initial evaluation of expressed channel function may be done via transfection in neonatal ventricular myocytes in culture. Promising constructs may be transfected into stem cells (Phase 2) which will then be tested for ability to couple to and pace cardiac myocytes in culture (Phase 3). In addition, promising constructs may be prepared as an adenovirus expressing the gene of interest and its function characterized in vitro (in cultures of neonatal and adult ventricular myocytes) and in vivo (in different cardiac regions). The in vivo studies may be done under Phase 5. The core function incorporates the preparation of adenoviral construct with a fluorescent marker and HCN, MiRP and mutant genes.

The specific goals or aims of Phase 1 are:
1. Expression and characterization of native HCN isoforms (pacemaker channel alpha subunits). HCN1, HCN2 and HCN4 can be over-expressed in neonatal myocytes and characterized in terms of kinetics, voltage dependence and autonomic modulation by isoproterenol (beta-adrenergic) and carbachol (muscarinic) as well as directly by cAMP. These studies can be done by transfection or adenovirus infection.
2. Functional impact of native HCN isoform over-expression. The effect of over-expression on automaticity of neonatal cultures can be determined for each isoform, as well as the susceptibility of rate to autonomic modulation. These studies can be done by adenovirus infection since they require high expression efficiency. Effect of each isoform on rate can be correlated with level of infection (i.e. multiplicity of infection [m.o.i.] employed) and corresponding mean current density for this m.o.i. (as measured under goal or aim 1).
3. Beta subunit modulation of pacemaker channel function and rate. Experiments under goals or aims 1 and 2 can be repeated (using adenovirus infection) with a range of HCN m.o.i. with and without co-infection by the HCN beta subunit MiRP1 (KCNE2). This will determine if the same effect can be achieved with an overall lower viral load by using KCNE2 to increase efficiency of HCN expression at the cell membrane. In addition, it will be determined if KCNE2 infection alone sufficiently upregulates endogenous HCN protein to significantly increase pacemaker current and spontaneous rate. If so, autonomic modulation of rate will again be determined.
4. Optimization of pacemaker genes. Mutated HCN genes can be tested in the neonatal ventricular cultures to identify those with improved characteristics in terms of kinetics, voltage dependence and autonomic sensitivity, and the effect of these mutated genes on rate will then be determined. Mutations that shift threshold voltage positive and speed kinetics will likely be most suitable.
5. Functional impact of gene expression in adult myocytes. Those gene products from goals or aims 1-4 that appear most promising in terms of biophysical characteristics and effect on spontaneous rate can be infected in adult ventricular and/or Purkinje cells in culture and the biophysical characteristics (which are likely to differ with the cell type in which the gene is expressed) and ability to generate pacemaker activity determined.
6. Regulation of expression. Those gene products (from goals or aims 1-5) that appear most promising will be tested by Phases 2 and 3 in stem cells and by Phase 5 in vivo. At the same time, they will also be transferred to new plasmids under the control of a regulatable (e.g. ecdysone-inducible) promoter. The regulatable constructs will be retested in vitro to assess the relation between expression level and induction of automaticity. Time course of regulation (i.e. time to up and down regulate channel expression) also will be determined (to be done in collaboration with Phase 2).
7. Current characterization after in vivo expression. In collaboration with Phase 5, after adenovirus infection of gene products in dog heart and ECG characterization, animals will be sacrificed, cells isolated from infected region, and pacemaker current characteristics determined.
8. Stem cell myocytes interaction. In collaboration with Phase 2 examine the required density of transfected stem cells to induce a higher pacing rate in neonatal myocyte cultures.

Phase 2: Creating A Biological Pacemaker Using Adult Mesenchymal Stem Cells

The goal is to optimize a pacemaker gene (or genes) and a delivery system (stem cells) to create a permanent regulatable pacemaker in a chosen cardiac region:

The specific goals or aims of Phase 2 are:
1. To study the membrane properties of adult mesenchymal stem cells.
2. To optimize a pacemaker gene or genes for transfection.
3. To transfect the stem cells with the chosen pacemaker gene under a constitutively active promoter using a bicistronic expression vector, which permits a gene of interest and EGFP to be translated from a single RNA (nearly 100% of cells that exhibit fluorescence also express the gene of interest). The vectors to be used are pCMS-EGFP vector for the expression of HCN genes, pHygEGFP as a cotransfection marker vector, pEGFP-C1 vector for the expression of HCN genes as fusion proteins with EGFP and pEGFP-1 vector for monitoring of transcription of EGFP from a muscle-specific promoter.
4. To use antibiotic selection markers to select stably transfected clones.
5. To study the membrane properties, and the expressed pacemaker current of the transfected stem cells.
6. To study the needle survival of transfected stem cells in vitro, and to compare these results to studies of survival post-injection in dogs performed in Phase 5.

7. Provide transfected stem cells to Phase 3 for coupling studies.
8. To study the membrane properties of adult heart cells (atrial, Purkinje and ventricular) in the absence and presence of coupling to stem cells, to determine whether, coupling induces pacing.
9. In collaboration with Phase 1, to examine the required density of transfected stem cells to induce a higher pacing rate in neonatal myocyte cultures.
10. In collaboration with Phase 5, after a stem cell pacemaker is implanted in a dog heart, the animals may be sacrificed at various times post implantation. One can dissociate the cells in Phase 2 and study their membrane properties, and also use biochemical markers to investigate their level of differentiation into cardiac cell types.
11. To transfect stem cells using a regulatable promoter (e.g. the ecdyson system)
12. Select for stable transfections by antibiotic resistance.
13. Test the dose-response relationship between the inducer and the level of pacemaker current expressed. Also, determine the lag between exposure to the inducer and pacemaker gene expression, and determine the lag between termination of inducer exposure and the decline in pacemaker gene expression.
14. Provide the construct for use in Phases 1 and 5 to perform similar studies as in goals or aims 9 and 10.

Phase 3: Integration of Myocytes and Stem Cells

To create a biological pacemaker from stem cells or repair damaged myocardium with a stem cell derived cardiogenic cell line, the new cells are to be integrated into the cardiac syncytium. This process uses the formation of gap junctions and the ability to pass from cell to cell 1) ions to initiate and propagate action potentials and 2) relevant second messengers to sustain normal physiologic function. The cardiac gap junctions are composed of some combination of three subunit proteins: connexin43 (Cx43), and/or Cx40, and/or Cx45. The major goals of this phase are to determine the types of connexins expressed and functioning in stem cells transfected with pacemaker genes for a biological pacemaker, and stem-cell derived cardiogenic cell lines which will be used for cardiac repair. One may also determine the ability of these cell types to form gap junctions with normal adult cardiac myocytes from nodal, atrial, Purkinje, and ventricular myocardium. If necessary or desirable, one can investigate transfection of either preparation with relevant connexin genes. Because both ionic permeability (assayed by measuring gap junctional conductance) and permeability to physiologic second messengers (assayed by larger molecular weight fluorescent dye permeation) are important, both measurements will be made in our experimental protocols.

Figure 4A:
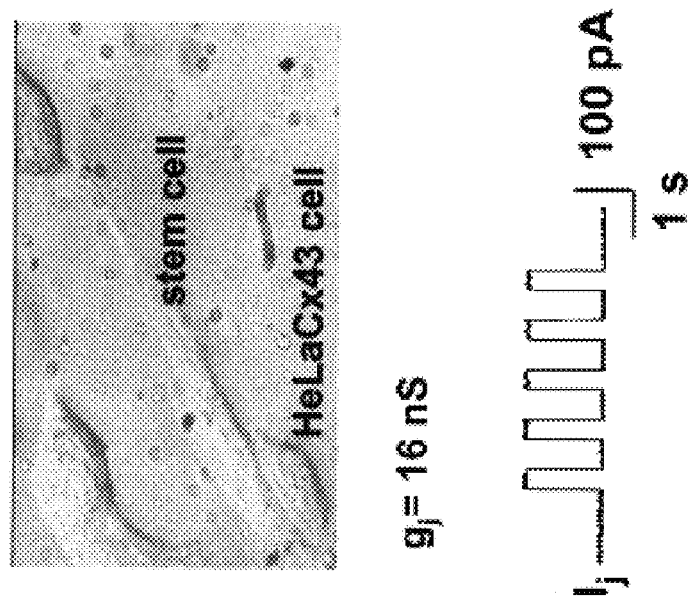
FIGS. 4A-B: stem cell coupling to HeLa cell transfected with Cx43. A: light micrograph and fluorescence micrograph of dye transfer from stem cell to HeLa cell. B: graph of ionic transfer between stem cell and HeLa cell.
Figure 4B:
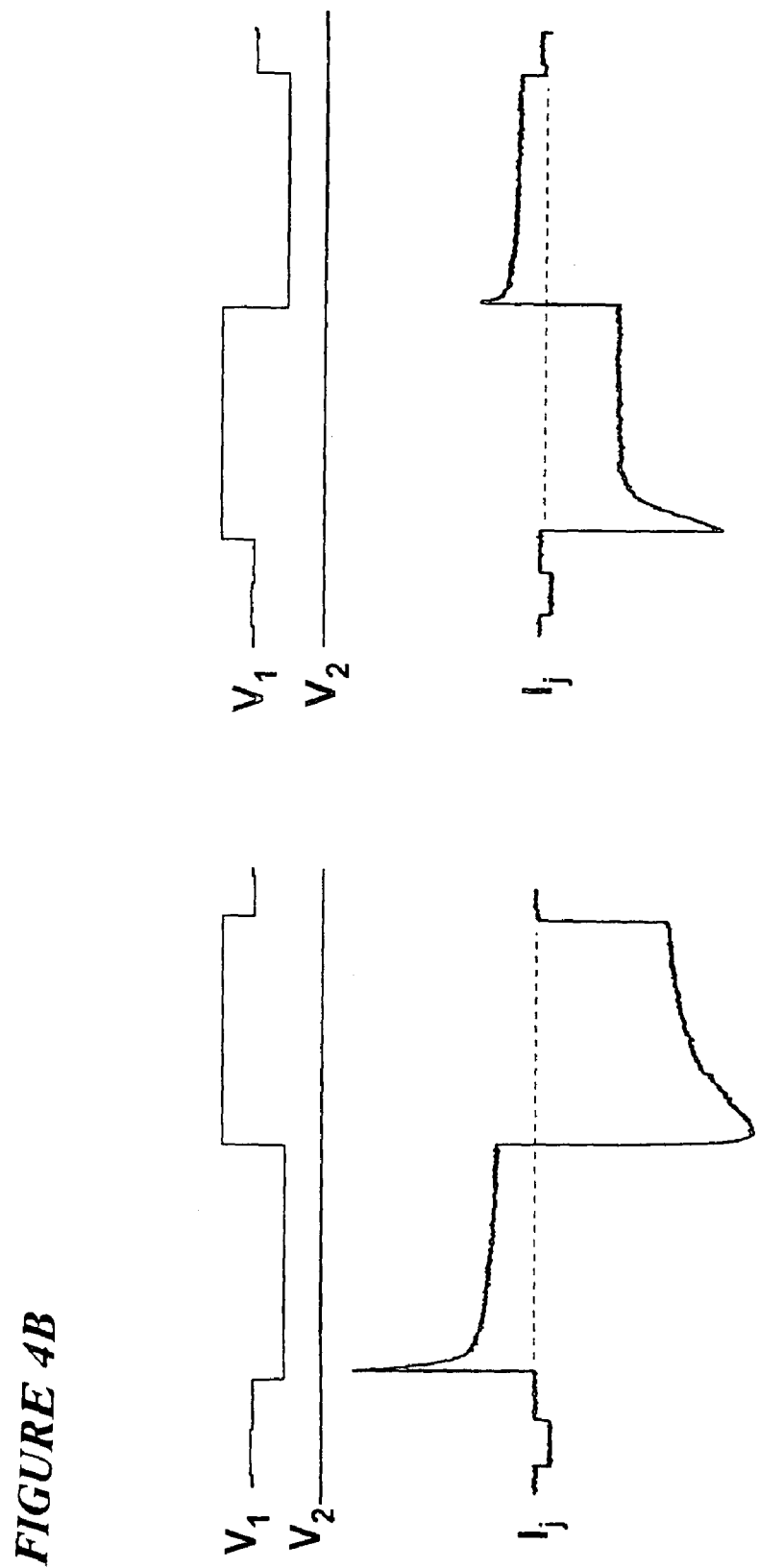
Figure 5A:
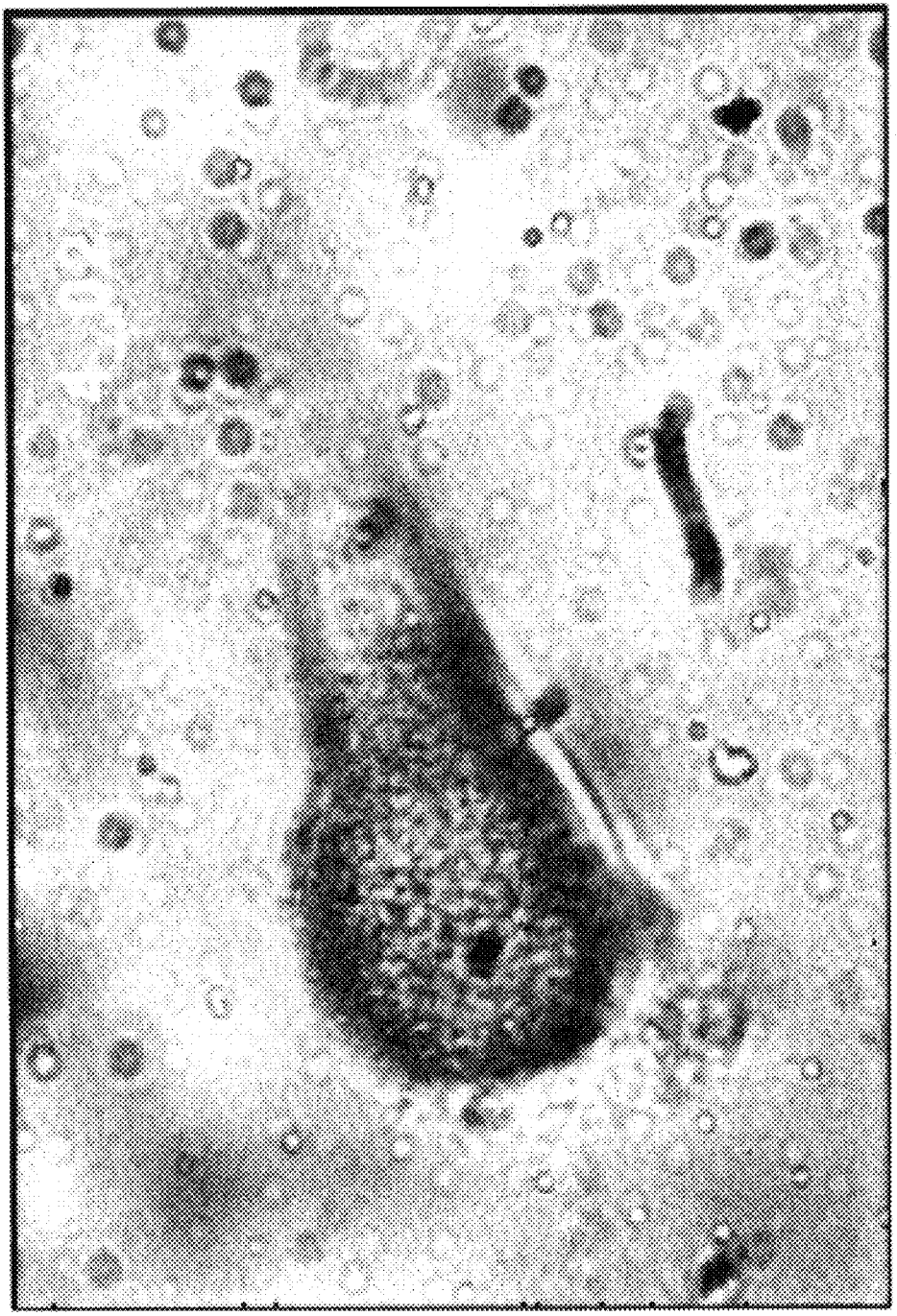
FIG. 5: I-V relationship of a human mesenchymal stem cell isolated from an embryoid body. A: light micrograph image of the stem cell isolated from an embryoid body. B: graph showing inward rectification suggesting the beginning of a cardiac-like differentiation for the I-V relationship.
Figure 5B:
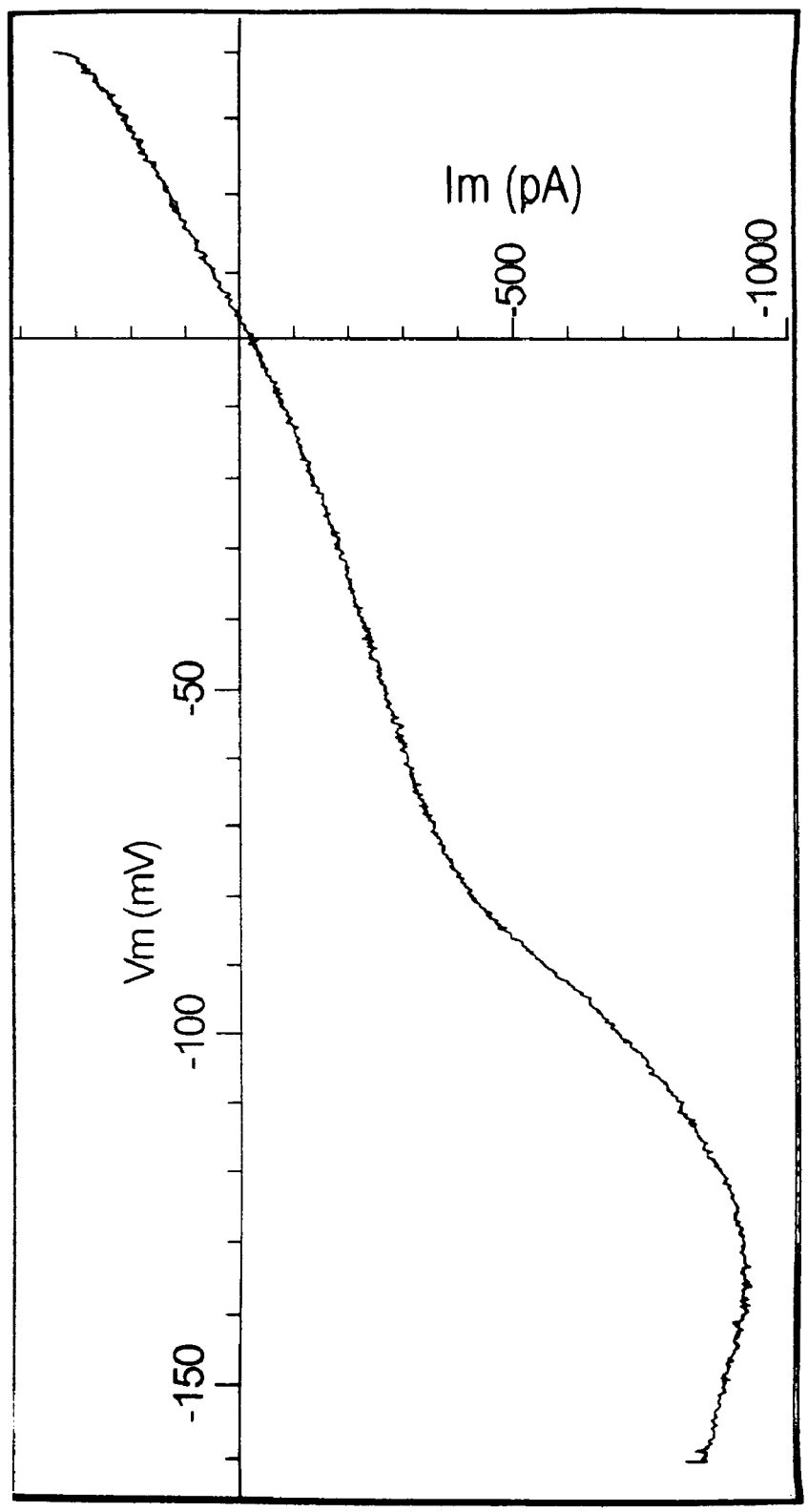
Figure 6:
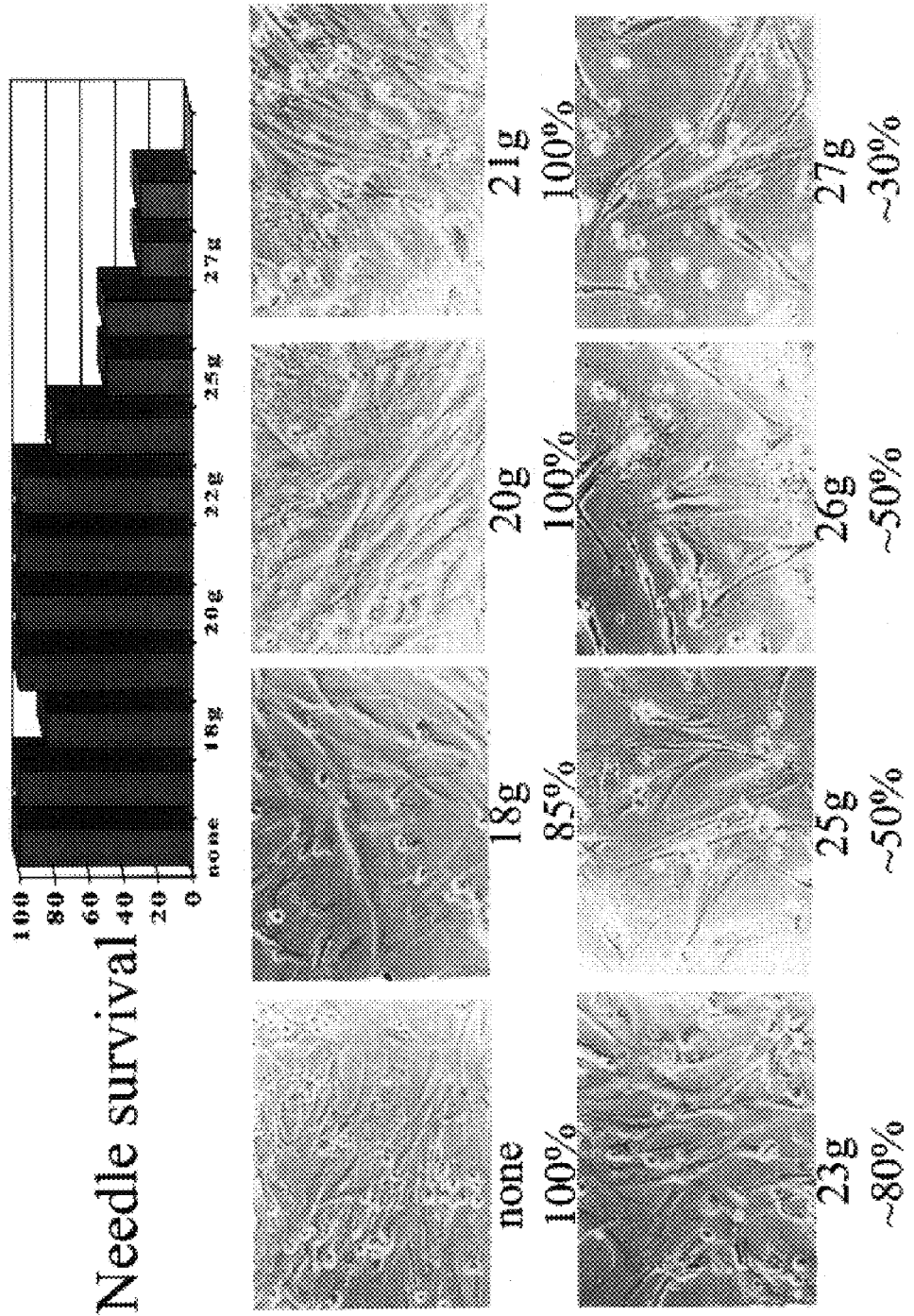
FIG. 6: needle survival rate of transfected stem cells in vitro.
Figure 8A:
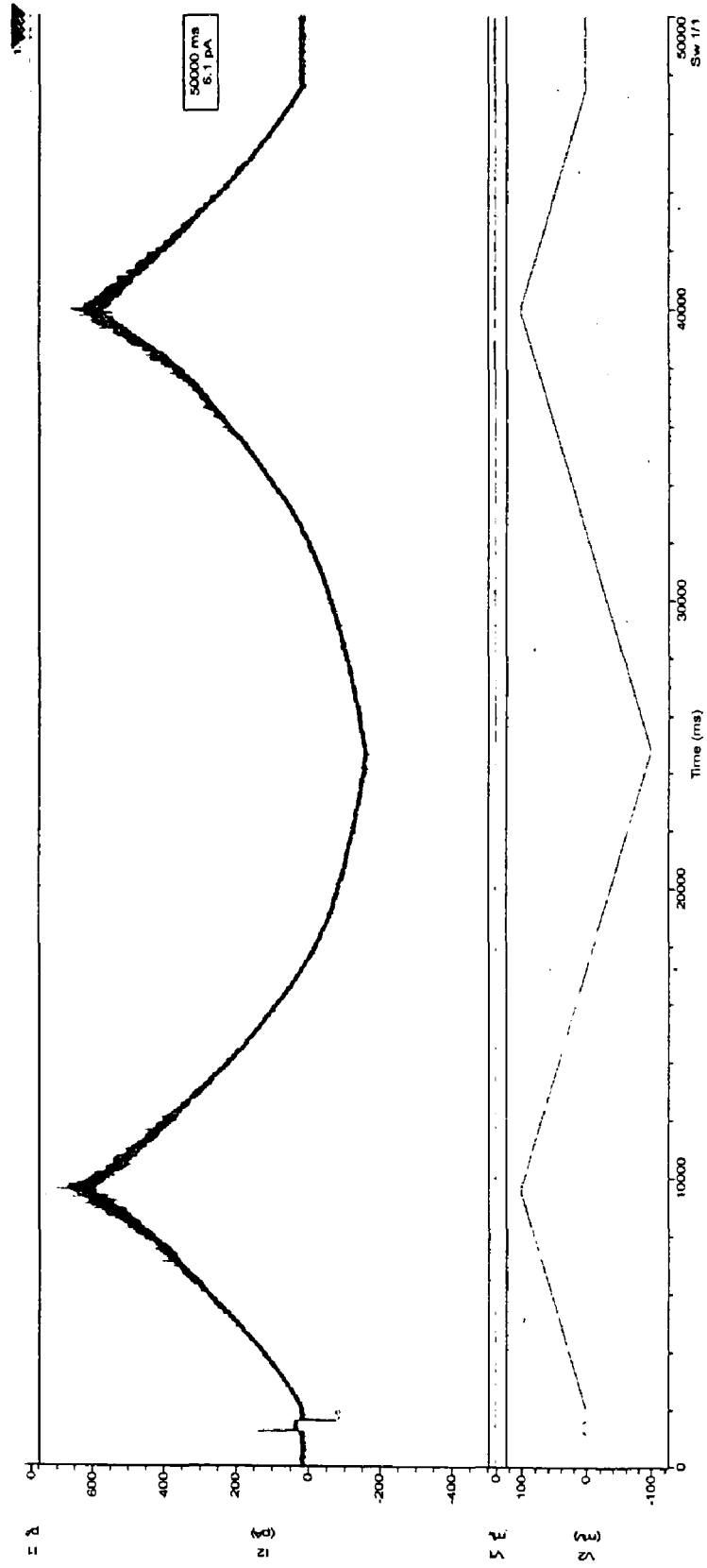
FIGS. 8A-B: HCN2 incorporated into stem cells can generate pacemaker current. A: ramp protocol of stem cells expressing HCN2. The ramp goes from +50 to −100 and back to 0 mV. B: step protocol of stem cells expressing HCN2. The steps are from 0 to −100 mV. Note that the experiment was done at room temperature, 20° C. Therefore, kinetics will be approximately 15× faster and amplitude will be 2× larger at physiologic temperature.
Figure 8B:
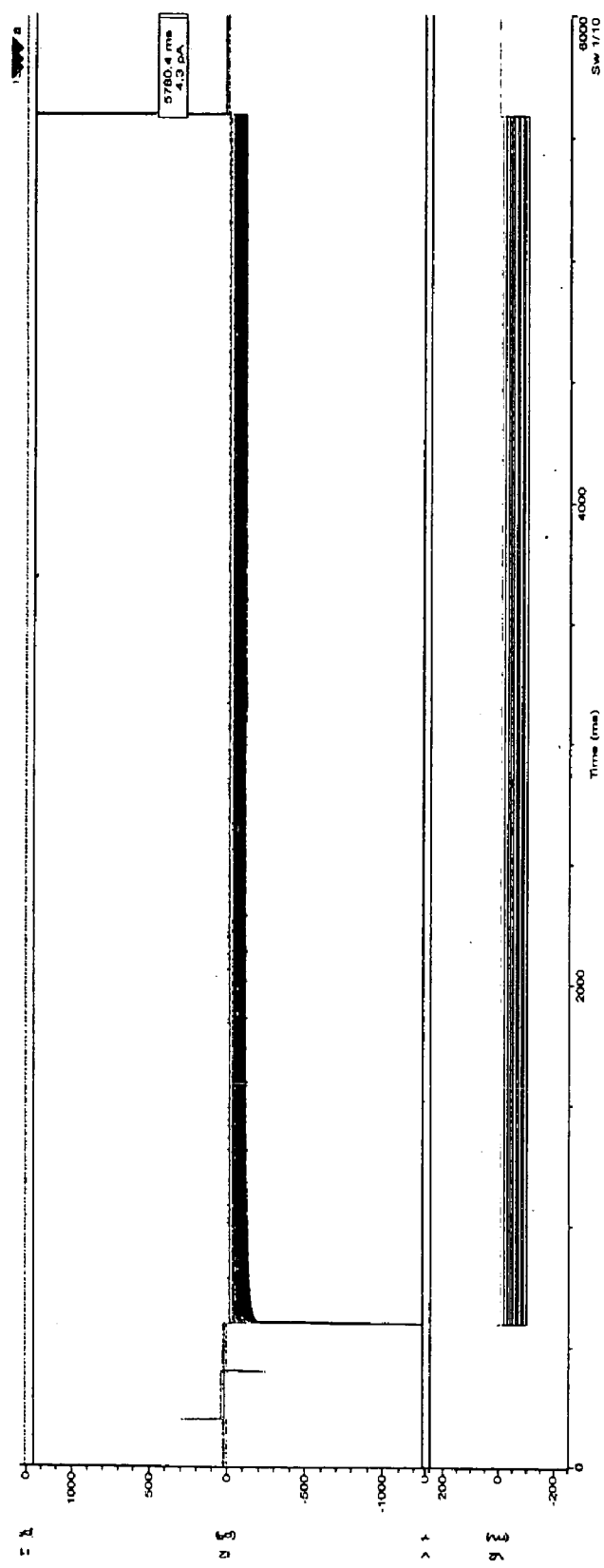
Figure 9A:
FIGS. 9A-B: HCN2 incorporated in a stem cell failed to generate pacemaker current. A: ramp protocol of stem cell failing to express HCN2. The ramp goes from +50 to −100 and back to 0 mV. B: Mutant HCN2 incorporated into a stem cell which failed to express and generate a current. The steps are from 0 to −100 mV. Note that the experiment was done at room temperature, 20° C. Therefore, kinetics will be approximately 15× faster and amplitude will be 2× larger at physiologic temperature.
Figure 9B:
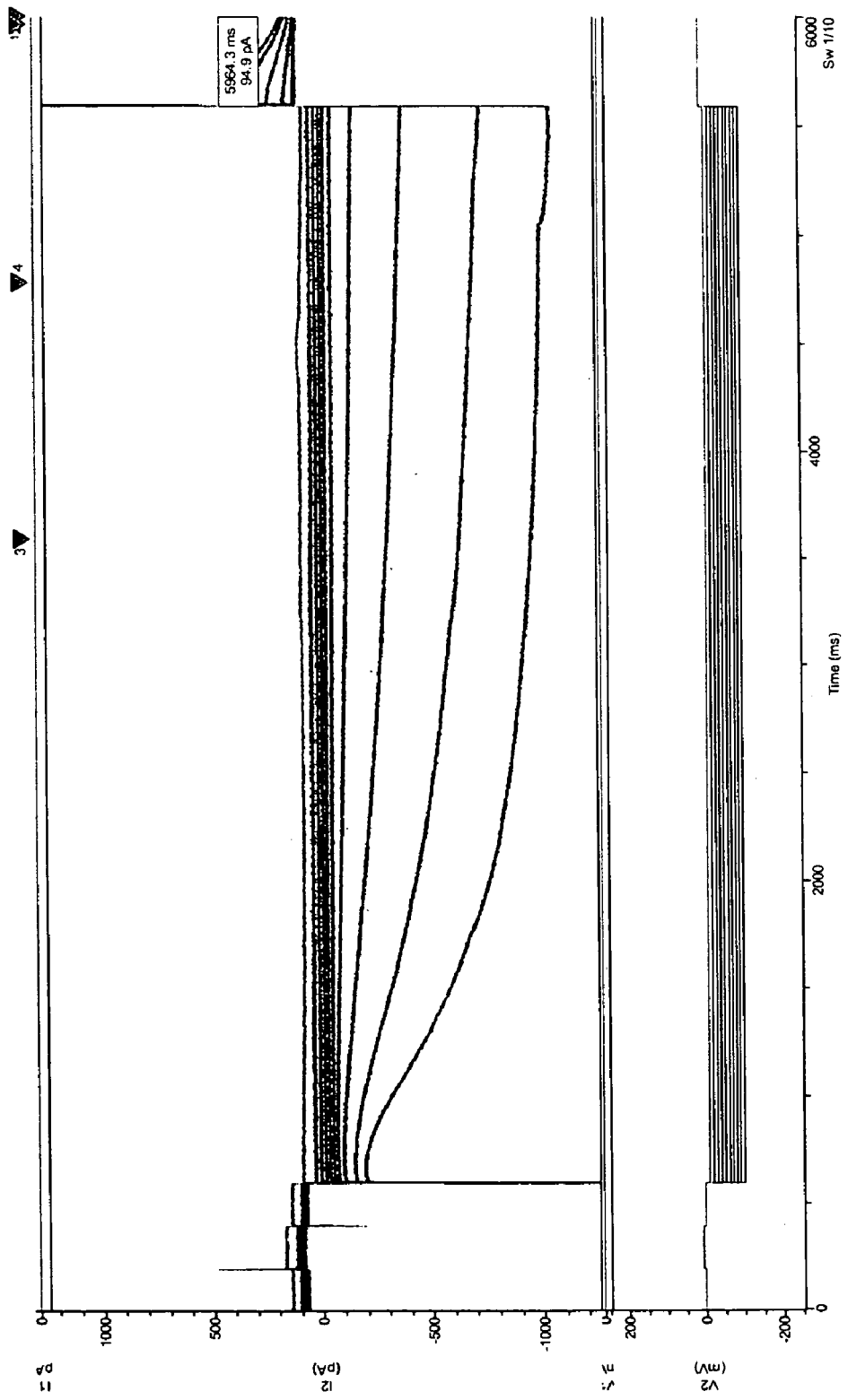
Figure 10A:
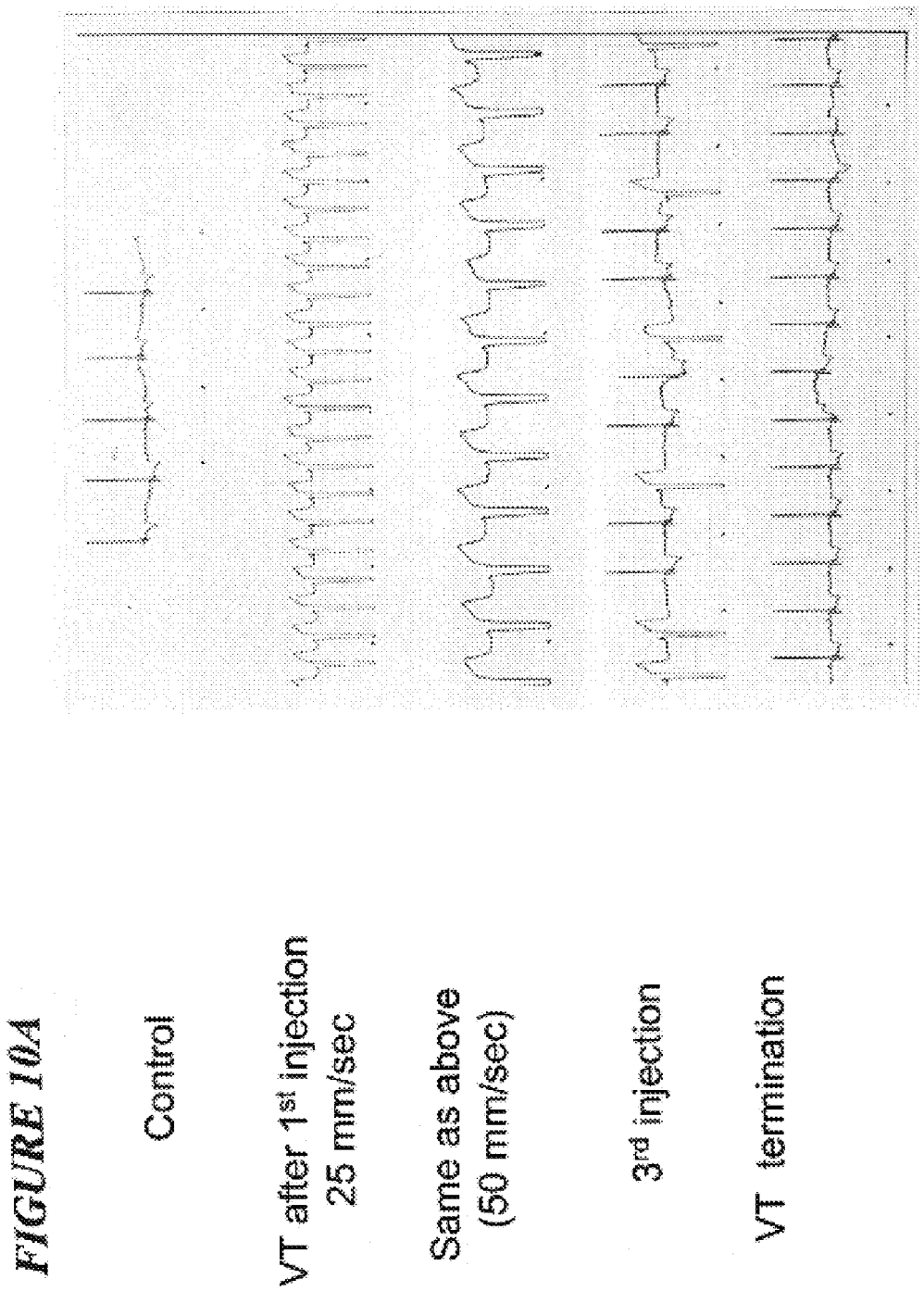
FIGS. 10A-E: Expression of pacemaker function in canine ventricle in situ as a result of implanting human mesenchymal stem cells having the HCN2 pacemaker gene. A dog was anesthetized and stem cells incorporating the HCN2 gene were implanted via a 21-gauge needle into the anterior left ventricular wall of the dog. A: recordings of ECGs demonstrating sinus rhythm and a ventricular tachycardia of a specific configuration based on stimulation by the needle insertion. B: vagal stimulation of the dog resulted in cessation of sinus rhythm. C: continued vagal stimulation brought onset of a stable idioventricular rhythm after cessation of sinus rhythm. This rhythm had the same configuration on ECG lead II as the rhythm that arose on the initial day of implantation (FIG. 10A) as a result of stimulation at the implantation site. The most likely cause of the idioventricular rhythm would be the initiation of spontaneous cardiac impulses by the pacemaker current in the stem cells. D: upon termination of vagal stimulation, the dog returned to sinus rhythm. E: dog's heart was removed and subjected to histological study slide displaying node-like structure of mesenchymal stem cells along the needle track of the implantation site.
Figure 10B:
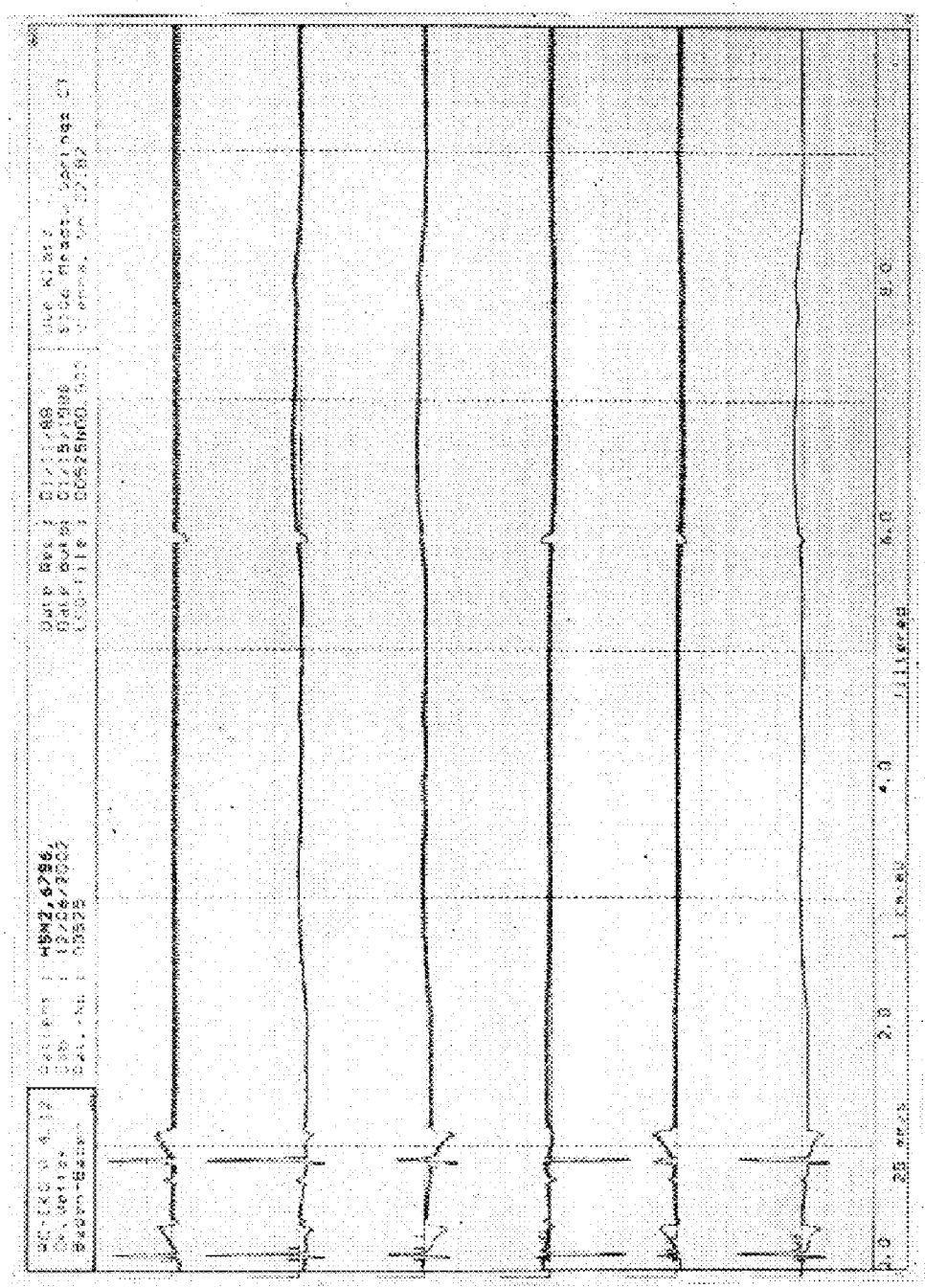
Figure 10C:
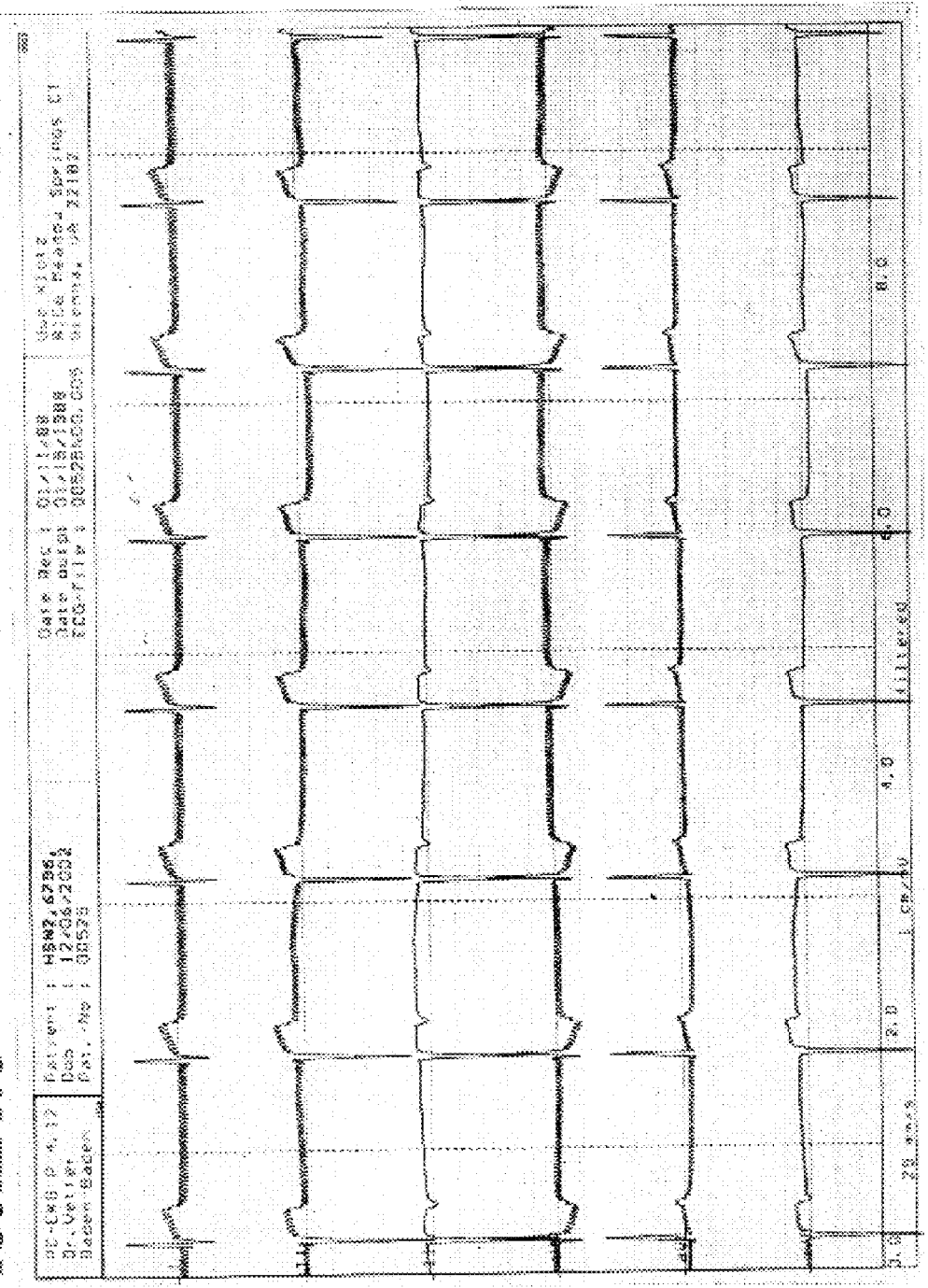
Figure 10D:
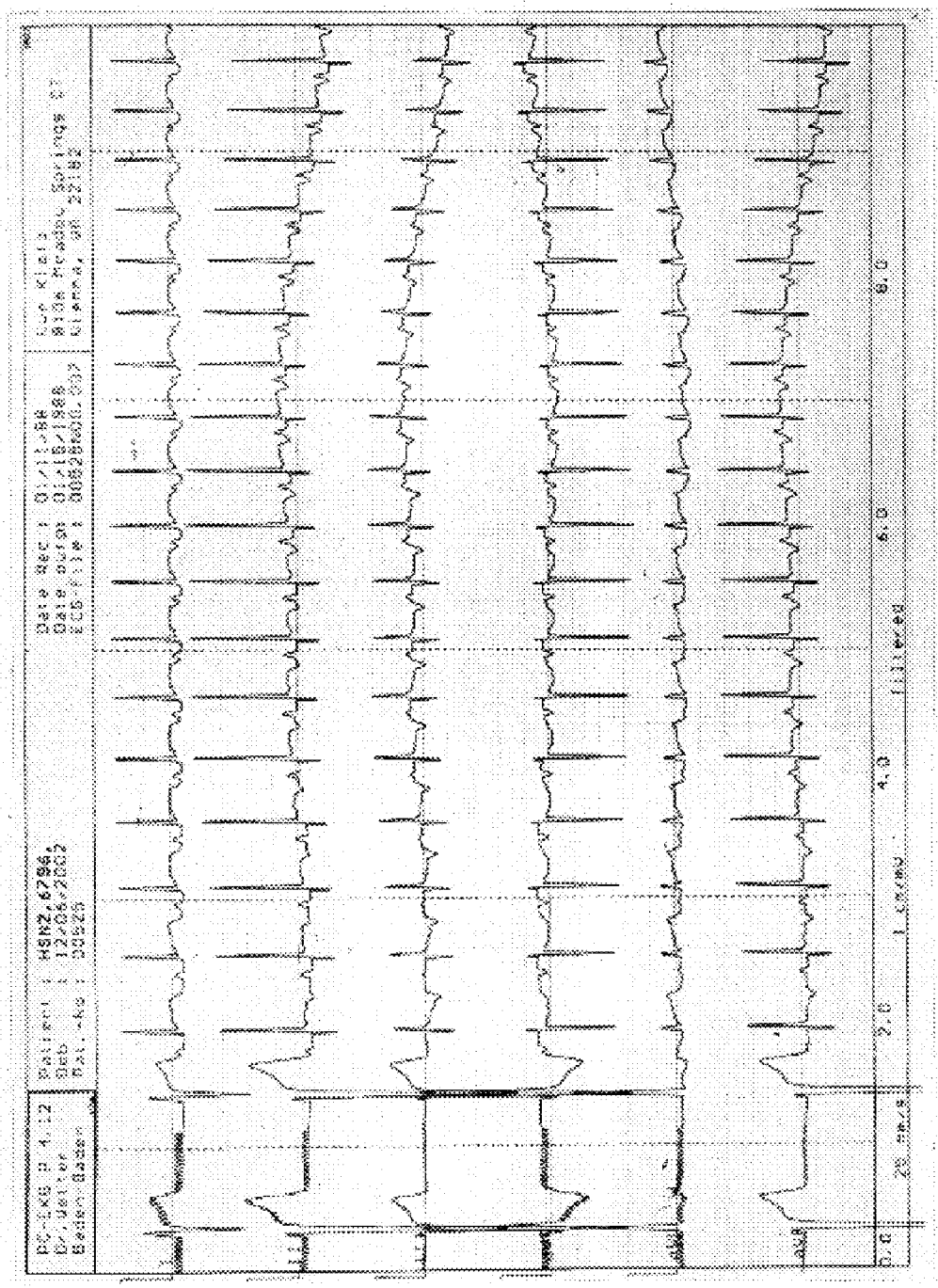
Figure 10E:
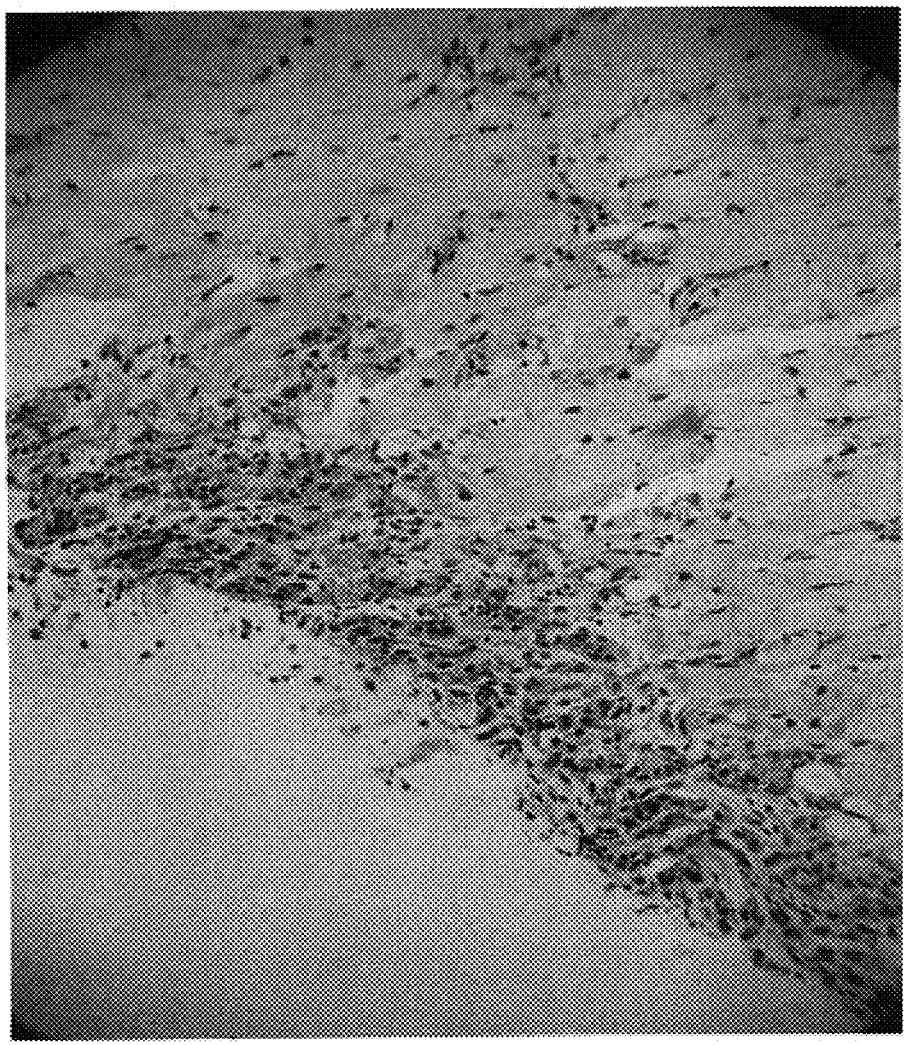

The specific goals or aims of Phase 3 are:
1. Determine the extent of stem cell coupling to cells (HeLa) transfected with cardiac connexins (40, 43, and 45). (see FIGS. 4A-B)
2. Determine the ability of stem cells to couple to adult cardiac myocytes from nodal regions, atrium, Purkinje fibers and ventricular myocardium.
3. Use immuno-localization to determine the distribution and location of Cx43, Cx40, and Cx45 in confluent stem cell cultures and co-cultures with cardiomyocytes.
4. For transfected stem cells with pacemaker genes repeat goals or aims 1-3.
5. Following implantation of transfected stem cells into myocardium at fixed time periods after the initiation of a biological pacemaker the animals will be sacrificed. In these animals, one can determine 1) which connexins are expressed in the mesenchymal stem cells and 2) the functional coupling in isolated cell pairs of stem cell to stem cell, and stem cell to cardiac myocyte.
6. Determine the extent of coupling between the cardiogenic cell line(s) to cultured cells (HeLa) expressing with cardiac connexins (40,43,45).
7. Determine the ability of the cardiogenic cell line(s) to couple to adult cardiac myocytes from the same regions as used in goal or aim 2.
8. Following implantation of cells from the cardiogenic cell line(s) in dogs for cardiac repair, at fixed time periods the animals will be sacrificed. One can determine from these animals 1) the expression of connexins in the repair cell line and 2) the functional coupling of cardiogenic cell line pairs, or pairs between adult cardiac cells and cells from the cardiogenic cell line.
9. Express connexins in stem cells, stem cells transfected with pacemaker genes, or stem cell derived cardiogenic cell line(s) as necessary or desirable. One can determine if improved functional coupling results.

Phase 4: Optimizing Stem Cells for Cardiac Repair

The goals of Phase 4 are (1) to grow stem cells for transformation into a cardiac cell line, (2) to select the cardiac cell lineage(s), (3) to further induce the cardiac-like cells to differentiate into ventricular or nodal cell types, and (4) to transfect each of the individual cell types with appropriate genes to optimize function and survival in particular cardiac regions, The specific goals or aims of Phase 4 are:
1. Transfect stem cells with a muscle or cardiac muscle specific promoter and green fluorescent protein to aid in selection of cells which grow along a cardiac lineage.
2. Select for stable transfections.
3. Test available approaches to induce cardiac differentiation (including embryoid bodies, 5-azacytidine exposure).
4. Select cells which have differentiated into a cardiogenic cell line.
5. Patch clamp the cells looking for a cardiac-like action potential and cardiac I-V relationship, and cardiac specific membrane currents.
6. Study the biochemical markers of cardiac differentiation.
7. Investigate whether trophic factors or co-culturing can induce further differentiation specifically to nodal type, atrial muscle or ventricular endocardium or epicardium. Again, test by patch clamping to look for signature membrane action potential or membrane currents.
8. Provide cells to Phase 3 for tests of coupling to adult myocytes from the desired cardiac region.
9. Test needle survival of each cell type.
10. Provide cells to Phase 5 for tests of efficacy in a dog cardiac model of heart failure. One can get cells back after experimental time period in vivo to study their properties.
11. Add new genes to optimize cell survival including an increased inward rectifier or gene to induce additional angiogenesis (like VEGF or other growth factors).

Phase 5: Expression of Pacemaker Function in the Intact Animal and in Isolated Tissues The overall goals of Phase 5 are: (1) to determine the extent to which specific pacemaker constructs expressed in vivo via the approaches of gene therapy and of stem cell implantation can affect cardiac rate and rhythm. (2) to determine the extent to which engineered cell lines can effect myocardial repair and AV nodal replacement.

The general hypotheses are (1) that pacemaker channels expressed or implanted in specific regions of the heart will develop regular, autonomic-responsive rhythms that counter the "clamping" effect of $I_{K1}$ in specialized conducting fibers and atrium and possibly ventricle, and (2) that engineered cell lines can replace non-functional myocardium or the AV node.

There are three goals or aims:

1. To investigate the function of specific HCN α and β subunit constructs as functioning pacemakers in the heart in situ and in isolated tissues, including testing of the following sub-hypotheses:
   a: Injection of adenoviral constructs carrying $HCN_2$ or $HCN_4$ into canine ventricular myocardium in vivo can elicit pacemaker current having characteristics of $I_f$. Although there is proof in concept that this will work, this intervention may not drive the ventricle because of the large $I_{K1}$ and the highly negative membrane potentials at which expressed $HCN_2$ is likely to activate.
   b: Injection of adenoviral constructs carrying $HCN_2$ or $HCN_4$ into canine bundle branches or atrium in vivo will elicit autonomic-responsive pacemaker current having characteristics of $I_f$, and—in light of the lesser $I_{K1}$ present and more positive activation of expressed HCN—capable of driving the heart.
   c: Injection of an adenoviral construct carrying MiRP1 into the above tissues in the absence of additional HCN isoforms can significantly upregulate endogenous $I_f$ and possibly speed activation kinetics as well, thus offering an alternative means for altering pacemaker function.
   d: Injection of an adenoviral construct of mutant genes (developed in Phases 1 and 2) will provide alternative and perhaps superior functional pacemakers.

2. To investigate the function of specific HCN α and β subunit constructs inserted into human mesenchymal cell lines to provide functional pacemakers to the heart in situ and in isolated tissues. The subhypotheses are modified from those above, as follows:
   a: Injection of stem cells carrying $HCN_2$ or $HCN_4$ into canine ventricular myocardium in vivo can elicit pacemaker current having characteristics of $I_f$ and capable of driving the heart. Stem cell implantation may make it possible to implant a node of sufficient dimension to overcome the effects of $I_{K1}$.
   b: Injection of stem cells carrying $HCN_2$ or $HCN_4$ into canine bundle branches or atrium in vivo will elicit autonomic-responsive pacemaker current having characteristics of $I_f$, and—in light of the lesser $I_{K1}$ present and more positive activation of expressed HCN—capable of driving the heart.
   c: Injection of stem cells carrying MiRP1 in the absence of additional HCN isoforms can significantly upregulate endogenous myocardial $I_f$ and possibly speed activation kinetics as well, thus offering an alternative means for altering pacemaker function.
   d: Injection of stem cells carrying constructs of mutant genes (developed in Phases 1 and 2) will provide alternative and perhaps superior functional pacemakers.

3. To investigate the utility of implantation of engineered cardiac cell lines in effecting myocardial repair. This includes replacement of myocardium and of AV node. The subhypotheses are:
   a: In canine hearts in which myocardial infarction has induced ventricular aneurysm alone and in hearts with congestive failure, cell lines engineered by Phase 4 will grow in the myocardium providing a substrate that is functional as studied hemodynamically and via imaging, while not generating arrhythmias. The result will be improved cardiac function and output.
   b: In canine hearts in which AV block has been induced via formalin injection or RF ablation, cell lines engineered by Phase 4 will provide bypass tracts that have the same function as the AV node in the heart in situ and in isolated tissues.

Stem Cell Isolation and Cell Culture

One can isolate and grow mesenchymal stem cells (human or canine) from human/canine bone marrow aspirates.

For example, 10 ml of marrow aspirate was collected into a syringe containing 6000 units of heparin to prevent clotting, washed twice in phosphate buffer solution (PBS), added to 20 ml of control medium (DMEM containing 10% FBS), and then centrifuged to pellet the cells and remove the fat. The cell pellet was resuspended in control medium and fractionated at 1100 g for 30 min on a density gradient generated by centrifugation of a 70% percoll solution at 13000 g for 20 minutes. The mesenchymal stem cell-enriched, low density fraction was collected, rinsed with control medium and plated at a density of $10^7$ nucleated cells per 60 $mm^2$ dish. The mesenchymal stem cells were then cultured in control medium at 37° C. in a humidified atmosphere containing 5% $CO_2$.

1) Mesenchymal Stem Cell Isolation and Characterization.

One can isolate hMSC and cMSC from donors. The advantages to using mesenchymal stem cells are that they do not require an endoderm for differentiation, are easy to culture, do not require an expensive cytokine supplement and have minimal immunogenecity. One can also test cell purity by flow cytometry and the ability of hMSC/cMSC to differentiate into osteogenic, chondrogenic, adipogenic and cardiogenic lineages.

For example, hMSC were transplanted into fetal sheep early in gestation, before and after the expected development of immunologic competence. The hMSC engrafted and persisted in multiple tissues for as long as 13 months after transplantation. Transplanted human cells underwent site-specific differentiation into chondrocytes, adipocytes, myocytes and cardiomyocytes, bone marrow stromal cells and thymic stroma. Unexpectedly, there was long-term engraftment even when cells were transplanted after the expected development of immunocompetence. A possible reason may be because hMSC express class I human leukocyte antigen but do not express class II, which may limit immune recognition.

In cardiac muscle, (human) β-2 microglobulin staining or in situ hybridization for human ALU sequences were combined with double staining with antibody against smooth endoplasmic reticulum ATPase-2 (SERCA-2), a cytoplasmic protein specific for smooth or skeletal muscle.

Cardiomyocytes have also been generated from murine marrow stromal cells. Murine bone marrow stromal cells were treated with 3 μM 5-azacytidine. After 1 week, some cells gradually increased in size to form a ball-like or stick-like appearance. After 2 weeks, the cells began spontaneously beating and the ball-like or stick-like cells connected with adjoining cells to form myotube-like structures. After 3 weeks, most of the synchronously beating cells connected and formed myotube-like structures and a cardiomyogenic cell line was formed.

Additionally, hMSC can be induced to differentiate in vitro exclusively to an osteogenic lineage with dexamethoasone, β-glycerol phosphate, ascorbate and 10% FBS. A chondrogenic lineage can be induced exclusively without serum, but with transforming growth factor β3 (in a pelleted micromass) and hMSC. Finally, an adipogenic lineage can be induced exclusively with 1-methyl 1-3-isobutylxanthine, dexamethasone, insulin, iodomethacin and hMSC.

In Vivo Demonstration of Cardiac Muscle Formation From Circulating Bone-Marrow Cells Normal and dystrophic (mdx) female mice received bone marrow transplantation (BMT) from normal male donor. After 70 days, histological sections of atrial and ventricular regions from BMT mice were probed for donor-derived Y chromosomes. In BMT-mdx mice single cardiomyocytes were found to contain bone-marrow derived Y chromosomes.

2) Tissue/Cell Culture.

One can prepare media for hMSC/cMSC and other cell types to be utilized in the project along with cell storage, growth and maintenance of cells in culture.

3) Morphometrics

One can utilize light, fluorescent, and confocal microscopy to monitor cell types and cardiogenic cell lines. The core may also support all histochemical and immuno-localization studies.

4) RNA Extraction and RT-PCR Analysis.

One can monitor the expression levels of all genes transfected into stem cells or cardiogenic cell lines.

Heart Failure Transplantation Therapy from hMSC

Transplantation therapy is also possible through the use of hMSC. After differentiation of the hMSC into cardiac myocytes, pure cultures are selected by cell survival or cell sorting (e.g. muscle or cardiac specific promoter driving antibiotic resistance gene or GFP). Then, one tests in vitro for electrical coupling of the differentiated myocytes to adult myocytes and also for biochemical, immunohistological and electrophysiological properties. After completion of these tests, one utilizes a canine model to evaluate integration of the differentiated myocytes into host tissue and improved contractile performance. The canine model is also examined for the absence of tumor formation or transmission of infectious agents. Then, methods of preventing rejection are tested. Note, that if the recipient and donor are the same, there is no danger of rejection. Finally, human trials are commenced.

Intercellular Delivery System for Small Molecules

The delivery of specific solutes to the intracellular compartment of functional syncytia can be achieved by seeding target tissues (cells) with stem cells that have been preloaded with a specified solute. Alternatively, a gene producing a small solute can be introduced into the stem cells as previously described. The transfer of solute from stem cells to target cells is via diffusion through gap junctions. The system is capable of delivering hydrophilic second messengers, drugs and their metabolites, and inorganic ions.

Figure 1B:
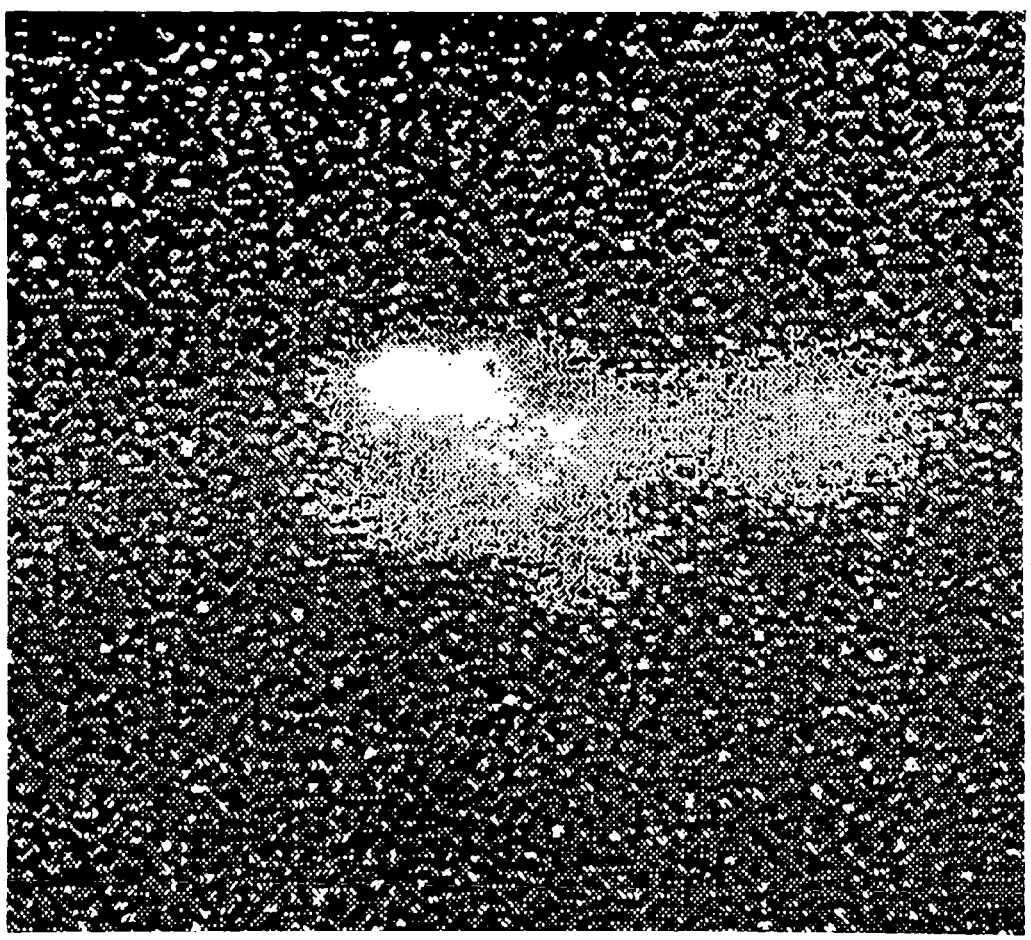

A) Loading of stems cells:

The loading of specific solutes into stem cells can be accomplished by electroporation or by perfusion of stem cells with media containing membrane permeable ester forms. FIG. 1a is a light micrograph of stem cells while FIG. 1b is of the same cells with fluorescence microscopy showing the presence of Lucifer Yellow (LY). The dye was loaded via electroporation.

Figure 2A:
FIGS. 2A-B: transfer of Lucifer Yellow dye from a stem cell to a HeLa cell transfected with Cx43. A: light micrograph image of stem cell loaded with Lucifer Yellow via electrode, with subsequent transfer to HeLa Cx43 cell. B: fluorescence image of same stem cell. Note that transfer of the dye presumably occurs by diffusion through gap junctions.
Figure 2B:
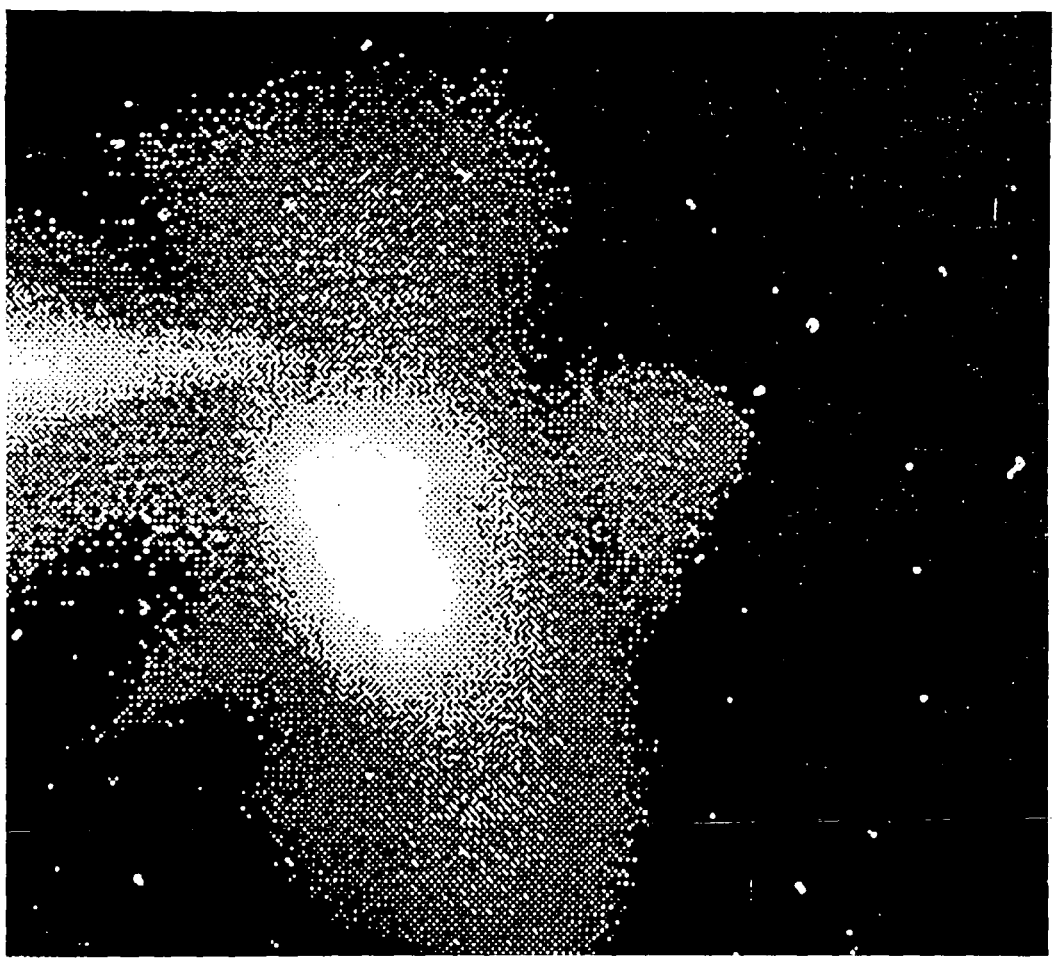

B) Transfer of loaded solute from stem cells to target cells: A demonstration using cells in culture. FIG. 2 shows transfer of dye from a stem cell to a HeLa cell. The LY has been delivered to the HeLa cell, presumably by diffusion through gap junctions.

Relevant parameters for the transfer:
1) Stem cells form gap junction channels with other cells b containing one or more of the following connexins: Cx43, Cx45, Cx40, Cx32 and Cx26.
2) Negatively charged solutes with minor diameters of ~1.0 nm are all able to transit the aforementioned gap junction channels (homotypic Cx43, Cx40, Cx45, heterotypic Cx43-Cx40 and mixed or heteromeric Cx43-Cx40)(63,64) and Cx32 and Cx26 (65).

The selectivity ratio for Lucifer Yellow relative to K+ is 0.025 for Cx43 and 0.0028 for Cx40. The type of gap junctions and total number of channels determine the rate of transit of a specific solute between stem cell and target cell.

Although one preferred embodiment of the invention is described, the invention is not so limited, as variations and modifications will occur to those skilled in the art.

The scope of the invention is determined by way of the appended claims.

REFERENCES

1. DiFrancesco D: The cardiac hyperpolarizing-activated current, $I_f$: Origins and developments. *Prog. BiophysMol. Biol.* Vol. 46, No. 3, 1985, pages 163-183.
2. Zhou Z and Lipsius SL: Effect of isoprenaline on $I_f$ current in latent pacemaker cells isolated from cat right atrium: ruptured vs. perforated patch whole-cell recording methods. *Pflugers Arch.* Vol. 423, No. 5 Pt. 6, June 1993, pages 442-447.
3. Thuringer D, et al.: A hyperpolarization-activated inward current in human myocardial cells. *J mol Cell. Cardiol.* Vol. 24, No. 5, May 1992, pages 451-455.
4. Porciatti F, et al.: Block of the pacemaker current $I_f$ in single human atrial myocytes and the effect of beta-adrenoceptor and A1-adenosine receptor stimulation. *Br J pharmacol.* Vol. 122, No. 6, February 1991, pages 963-969.
5. Yu H, et al.: Pacemaker current exists in ventricular myocytes. *Circ. Res.* Vol. 72, No. 1, January 1993, pages 232-236.
6. Cerbai E, et al.: The properties of the pacemaker current $I_f$ in Human Ventricular Myocytes are modulated by Cardiac Disease. *J mol. Cell Cardiol.* Vol. 33, No. 3, March 2001, pages 441-448.
7. DiFrancesco D: Generation and control of cardiac pacing: the pacemaker current. *Tends Cardiovasc. Med.* Vol. 1, 1991, pages 250-255.
8. Robinson R B, et al.: Developmental change in the voltage dependence of the pacemaker current, $I_f$, in rat ventricle cells. *Pflugers Arch.* Vol. 433, 1991, pages 533-535.
9. Fares N, et al.: Characterization of a hyperpolarization-activated current in dedifferentiated adult rat ventricular cells in primary culture. *J. Physiol.* Vol. 506, No. 1, Jan. 1, 1998, pages 73-82.
10. Cerbai E, et al.: Influence of postnatal-development on $I_f$ occurrence and properties in neonatal rat ventricular myocytes. *Cardiovasc. Res.* Vol. 42, No. 2, May 1999, pages 416-423.
11. Cerbai E, et al.: Characterization of the hyperpolarization-activated current, $I_f$, in ventricular myocytes isolated from hypertensive rats. *J. Physiol. Vol.* 481, No. 3, Dec. 15, 1994, pages 585-591.
12. Cerbai E, et al.: Characterization of the hyperpolarization-activated current, $I_f$, in ventricular myocytes from human failing heart. *Circulation.* Vol. 95, No. 3, Feb. 4, 1997, pages 568-571.
13. Santoro B, et al.: Interactive cloning with the SH3 domain of N-src identifies a new brain specific ion channel protein, with homology to Eag and cyclic nucleotide-gated channels. *Proc. Natl. Scd. USA*. Vol. 94, No. 26, Dec. 23, 1997, pages 14815-14820.

14. Ludwig A, et al.: A family of hyperpolarization-activated mammalian cation channels. *Nature*. Vol. 393, No. 6685, Jun. 11, 1998, pages 587-591.

15. Santoro B, et al.: Identification of a gene encoding a hyperpolarization-activated pacemaker channel of brain. *Cell*. Vol. 93, No. 5, May 29, 1998, pages 717-729.

16. Shi W, et al.: Distribution and Prevalence of hyperpolarization-activated cation channel (HCN) mRNA Expression in Cardiac Tissues. *Circ. Res*. Vol. 85, No. 1, Jul. 9, 1999, pages e1-e6.

17. Ishii T M, et al.: Molecular characterization of the hyperpolarization-activated cation channel in rabbit heart sinoatrial node. *J. Biol. Chem*. Vol. 264, No. 18, Apr. 30, 1999, pages 12835-12839.

18. Ludwig A, et al.: Two pacemaker channels from human heart with profoundly different activation kinetics. *EMBO J*. Vol. 18, No. 9, May 4, 1999, pages 2323-2329.

19. Moosmang S, et al.: Cellular expression and functional characterization of four hyperpolarization-activated pacemaker channels in cardiac and neuronal tissues. *Eur. J. Biochem*. Vol. 268, No. 6, March 2001, pages 1646-1652.

20. Altomare C, et al.: Allosteric voltage-dependent gating of HCN channels. *Biophys. J*. Vol. 80, 2001, page 241a.

21. Protas L, et al.: Chronic neuropeptide Y exposure increases L-type Ca current in neonatal rat cardiomyocytes. *Am. J. Physiol*. Vol. 277, No. 3 Pt. 2, September 1999, pages H940-H946.

22. Kuznetsov V, et al.: β 2-adrenergic receptor actions in neonatal and adult rat ventricular myocytes. *Circ. Res*. Vol. 76, No. 1, January 1995, pages 40-52.

23. Ellingston O, et al.: Adult rat ventricular myocytes cultured in defined medium: phenotype and electromechanical function. *Am. J. Physiol*. Vol. 265, No. 2 Pt. 2, August 1993, pages H747-H754.

24. Ng P, et al.: An enhanced system for construction of adenoviral vectors by the two-plasmid rescue method. *Hwn.Gene Ther*. Vol. 11, No. 5, Mar. 20, 2000, pages 693-699.

25. He T C, et al.: A simplified system for generating recombinant adenoviruses. *Proc. Natl. Acad. Sci. USA*. Vol. 95, No. 5, Mar. 3, 1998, pages 2509-2514.

26. Santoro B, et al.: The HCN gene family: molecular basis of the hyperpolarization-activated pacemaker channels. *Ann. NY Acad. Sci*. Vol. 868, Apr. 30, 1999, pages 741-764.

27. Accili E A, et al.: Properties and modulation of $I_f$ in newborn versus adult cardiac SA node. *Am. J. Physiol*. Vol. 272, 1991, pages H1549-H1552.

28. Qu J, et al.: Sympathetic innervation alters activation of pacemaker current ($I_f$) in rat ventricles. *J. Physiol*. Vol. 526, No. 3, Aug. 1, 2000, pages 561-569.

29. Cui J, et al.: Gating of $I_{SK}$ expressed in Xenopus oocytes depends on the amount of mRNA injected. *Gen. Physiol*. Vol. 104, No. 1, July 1994, pages 87-105.

30. Guillemare E, et al.: Effects of the level of mRNA expression on biophysical properties, sensitivity to neurotoxins, and regulation of the brain delayed-rectifier K+ channels Kv1.2. *Biochemistry*. Vol. 31, No. 49, Dec. 15, 1992, pages 12463-12468.

31. Honore E, et al.: Different types of K+ channel current are generated by different levels of a single mRNA. *EMBO J*. Vol. 11, No. 7, July 1992, pages 2465-2471.

32. Moran O, et al.: Level of expression controls modes of gating of a K+ channel. *FEBS Lett*. Vol. 302, No. 1, May 4, 1992, pages 21-25.

33. DiFrancesco D, et al.: Direct activation of cardiac pacemaker channels by intracellular cyclic AMP. *Nature*. Vol. 351, No. 6322, May 9, 1991, pages 145-147.

34. Kaupp U B, et al.: Molecular diversity of pacemaker ion channels. *Annu. Rev. Physiol*. Vol. 63, 2001, pages 235-257.

35. Chang F, et al.: Effects of protein kinase inhibitors on canine Purkinje fibre pacemaker depolarization and the pacemaker current $I_f$. *J. Physiol*. Vol. 440, 1991, pages 367-384.

36. Yu H, et al.: Phosphatase inhibition by calyculin A increases $I_f$ in canine Purkinje fibers and myocytes. *Pflugers Arch*. Vol. 422, No. 6, March 1993, pages 614-616.

37. Accili E A, et al.: Differential control of the hyperpolarization-activated current ($I_f$) by intracellular cAMP and phosphatase inhibition. *J. Physiol*. Vol. 491, 1996, pages 115.

38. Ranjan P, et al.: Mechanism of anode break stimulation in the heart. *Biophys. J*. Vol. 74, No. 4, April 1998, pages 1850-1863.

39. Moroni A, et al.: Kinetic and ionic properties of the human HCN2 pacemaker channel. *Pflugers Arch*. Vol. 439, No. 5, March 2000, pages 618-626.

40. Santoro B, et al.: Molecular and functional heterogeneity of hyperpolarization-activated pacemaker channels in the mouse CNS. *J Neurosci*. Vol. 20, No. 14, Jul. 15, 2000, pages 5264-5275.

41. Shi W, et al.: The distribution and prevalence of HCN isoform in the canine heart and their relation to the voltage dependence of $I_f$. *Biophys. J*. Vol. 78, 2000, page 353A.

42. Melman Y F, et al.: Structural determinants of KvLQT1 control by the KCNE family of proteins. *J Biol Chem*. Vol. 276, No. 9, Mar. 2, 2001, pages 6439-6444.

43. Tinel N, et al.: KCNE2 confers background current characteristics to the cardiac KCNQ1 potassium channel. *EMBO J*. Vol. 19, No. 23, Dec. 1, 2000, pages 6326-6330.

44. Martens J R, et al.: Differential targeting of Shaker-like potassium channels to lipid rafts. *Biol. Chem*. Vol. 275, No. 11, Mar. 17, 2000, pages 7443-7446.

45. Chauhan V S, et al.: Abnormal cardiac Na(+) channel properties and QT heart rate adaptation in neonatal ankyrin (B) knockout mice. *Circ. Res*. Vol. 86, No. 4, Mar. 3, 2000, pages 441-447.

46. Walsh K B, et al.: Distinct voltage-dependent regulation of heart-delayed $I_K$ by protein kinases A and C. *Am. J. Physiol*. Vol. 261, No. 6 Pt. 1, December 1991, pages C1081-C1090.

47. Gerhardstein B L, et al.: Proteolytic processing of the C terminus of the alpha (1C) subunit of L-type calcium channels and role of a proline-rich domain in membrane tethering of proteolytic fragments. *J Biol. Chem*. Vol. 275, No. 12, Mar. 24, 2000, pages 8556-8563.

48. Barbuti A, et al.: Action of internal pronase on the f-channel kinetics in the rabbit SA node. *J. Physiol*. Vol. 520, No. 3, Nov. 1, 1999, pages 737-744.

49. Wainger B J, et al.: Domains involved in cyclic nucleotide modulation of hyperpolarization-activated HCN channels. *Nature*. In Press, 2001.

50. Wahler G M: Developmental increases in the inwardly rectifying potassium current of rat ventricular myocytes. *Am. J. Physiol*. Vol. 262, No. 5 Pt. 1, May 1992, pages C1266.

51. Abbott G W, et al.: MiRP1 forms $I_{Kr}$ potassium channels with HERG and is associated with cardiac arrhythmia. *Cell*. Vol. 97, No. 2, Apr. 16, 1999, pages 175-187.

52. Sanguinetti M C, et al.: Coassembly of KvLGQT1 and minK ($I_{SK}$) proteins to form cardiac $I_{SK}$ potassium channels. *Nature*. Vol. 384, No. 6604, Nov. 7, 1996, pages 80-83.

53. Dixon J E and McKinnon D: Quantitative analysis of potassium channel expression in atrial and ventricular muscle of rats. *Circ. Res*. Vol. 75, No. 2, August 1994, pages 252-260.

54. Sclagger H and von Jagow G: Tricine-sodium dodecyl sulfate-polyacrylamide gel electrophoresis for separation of proteins in the range from 1 to 100 Kda. *Analytical Biochem*. Vol. 166, No. 2, Nov. 1, 1987, pages 368-379.

55. Hansen J E, et al.: Prediction of O-glycosylation of mammalian proteins: Specificity patterns of UDP-GalNAc: polypeptide N-acetylgalactosaminyltransferase. *Biochem. J*. Vol. 308, No. 3, Jun. 15, 1995, pages 801-813.

56. Vassalle M, et al.: Pacemaker channels and cardiac automaticity In "Cardiac Electrophysiology. From Cell to Bedside", Eds. Zipes D and Jalife W B Saunders Co. Philadelphia, Pa., 2000, pages 94-103.

57. Rosen, M. R. and Robinson R. B.: Heart rate: a simple yet complex concept. *Dialogues in Cardiovascular Medicine*. Vol. 6, No. 1, 2001, pages 2-19.

58. Yu, H. et al.: MinK-Related Peptide 1: A β Subunit for the HCN Ion Channel Subunit Family Enhances Expression and Speeds Activation. *Circ. Res*. Vol. 88, 2001, pages 84-87.

59. Qu, J. et al.: Functional comparison of HCN isoforms expressed in ventricular and HEK 293 cells. *Pfulgers Arch.—Eur. J. Physiol*. Vol. 444, 2002, pages 597-601.

60. Qu, J. et al.: Sympathetic innervation alters activation of pacemaker current ($I_f$) in rat ventricle. *J. of Physiol*. Vol. 526, No. 3, 2000, pages 561-569.

61. Hamm, A. et al.: Efficient Transfection Method for Primary Cells. *Tissue Engineering*. Vol. 8, No. 2, 2002, pages 235-245.

62. Qu, J. et al.: HCN2 Overexpression in Newborn and Adult Ventricular Myocytes. *Circ. Res*. Vol. 89, 2001, pages 8-14.

63. Valiunas, V. et al.: Cardiac gap junction channels show quantitative differences in selectivity. *Circ. Res*. Vol. 91, No. 2, 2002, pages 104-111.

64. Valuinas, V.: Biophysical properties of connexin-45 gap junction hemichannels studied in vertebrate cells. *J. Gen. Physiol*. Vol. 119, No. 2, 2002, pages 147-164.

65. Cao, F. et al.: A quantitative analysis of connexin-specific permeability differences of gap junctions expressed in HeLa transfectants and Xenopus oocytes. *J. Cell Sci*. Vol. 111 (pt.1), 1998, pages 31-43.

What is claimed:

1. A composition for delivery to a mammalian heart comprising an isolated mesenchymal stem cell incorporated with a nucleic acid encoding at least one hyperpolarization-activated, cyclic nucleotide-gated (HCN) channel, the HCN-encoding region being functionally linked to a promoter, wherein the nucleic acid encoding the at least one HCN channel is expressed, wherein the mesenchymal stem cell further comprises a nucleic acid molecule encoding a MiRP1 polypeptide.

2. A method of expressing at least one pacemaker ion channel in a mammalian heart, wherein the at least one pacemaker ion channel is a hyperpolarization-activated, cyclic nucleotide-gated (HCN) channel, comprising (a) preparing the composition of claim 1; and (b) directly administering the composition of claim 12 to the mammalian heart.

3. The method of claim 2, wherein the nucleic acid encoding at least one HCN channel encodes a HCN2 channel.

4. A method for inducing a pacemaker current in a subject's heart comprising: (a) preparing the composition of claim 1; and (b) administering the composition of claim 12 directly to the heart, wherein expression of the pacemaker ion channel in the mesenchymal stem cell generates a pacemaker current in the heart.

5. The method of claim 4, wherein the nucleic acid encoding at least one HCN channel encodes a HCN2 channel.

6. The method of claim 4, wherein the nucleic acid encodes a HCN1 channel.

7. An isolated mesenchymal stem cell transformed with a nucleic acid encoding at least one pacemaker ion channel, wherein the at least one pacemaker ion channel is a hyperpolarization-activated, cyclic nucleotide-gated (HCN) channel, and wherein the nucleic acid encoding the at least one pacemaker ion channel is expressed, wherein the mesenchymal stem cell further comprises a nucleic acid molecule encoding a MiRP1 polypeptide.

8. The mesenchymal stem cell of claim 7, wherein the nucleic acid encoding at least one pacemaker ion channel encodes a HCN2 channel.

9. The composition of claim 1, wherein the nucleic acid encoding at least one HCN channel encodes a HCN2 channel.

10. The mesenchymal stem cell of claim 7, wherein the nucleic acid encoding at least one pacemaker ion channel encodes a HCN1 channel.

11. The composition of claim 1, wherein the nucleic acid encoding at least one HCN channel encodes a HCN1 channel.

12. The method of claim 2, wherein the nucleic acid encoding at least one HCN channel encodes a HCN1 channel.

13. The mesenchymal stem cell of claim 7, wherein the nucleic acid encoding at least one pacemaker ion channel encodes a HCN4 channel.

14. The composition of claim 1, wherein the nucleic acid encoding the at least one HCN channel encodes a HCN4 channel.

15. The method of claim 2, wherein the nucleic acid encoding at least one HCN channel encodes a HCN4 channel.

16. The method of claim 4, wherein the nucleic acid encodes a HCN4 channel.

* * * * *